United States Patent [19]
Dawson et al.

[11] Patent Number: 5,637,492
[45] Date of Patent: Jun. 10, 1997

[54] ACTIVATABLE FIBRINOLYTIC AND ANTI-THROMBOTIC PROTEINS

[75] Inventors: Keith Dawson, Marlow; Richard M. Edwards, Thame; Joan M. Forman, Oxford, all of United Kingdom

[73] Assignee: British Biotech Pharmaceuticals, England

[21] Appl. No.: 854,603

[22] PCT Filed: Dec. 7, 1990

[86] PCT No.: PCT/GB90/01912
§ 371 Date: Jun. 4, 1992
§ 102(e) Date: Jun. 4, 1992

[87] PCT Pub. No.: WO91/09118
PCT Pub. Date: Jun. 27, 1991

[30] Foreign Application Priority Data

Dec. 7, 1989 [GB] United Kingdom ............... 8927722

[51] Int. Cl.⁶ .............. A61K 37/48; C12N 9/68; C12N 15/59

[52] U.S. Cl. ............ 435/217; 435/212; 435/172.3; 424/94.64

[58] Field of Search .............. 435/69.1, 172.3, 435/214, 217, 212, 226, 193; 530/384, 381; 424/94.63, 94.64

[56] References Cited

U.S. PATENT DOCUMENTS 5,200,340  4/1993  Forster et al. .................. 424/94.64

Primary Examiner—Dian C. Jacobson
Attorney, Agent, or Firm—Banner & Witcoff, Ltd.

[57] ABSTRACT

Proteinaceous compounds are activatable by enzymes of the clotting cascade to have fibrinolytic or clot formation inhibition activity. For example, a plasminogen analogue is activatable to plasmin by thrombin or Factor Xa. Fibrinolytic or clot formation inhibition activity is therefore directed to the site of clot formation.

24 Claims, 15 Drawing Sheets

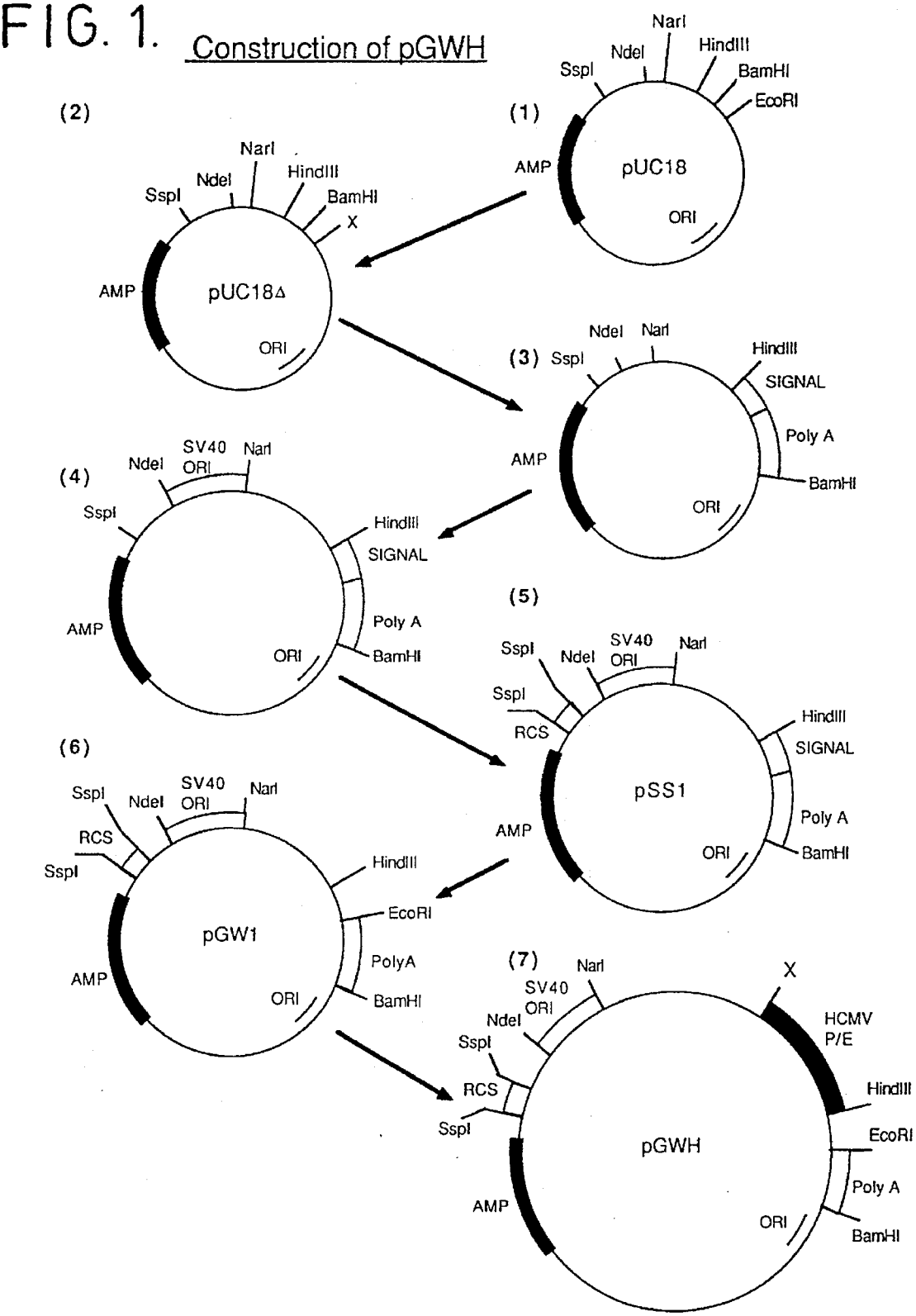
FIG. 1. Construction of pGWH

FIG. 2A

Plasminogen cDNA and amino acid sequence

```
                                                            BalI
GATGTAAGTCAACAACATCCTGGGATTGGGACCCACTTTCTGGGCACTGCTGG^CCAGTCC
    10        20        30        40        50        60

>Signal sequence
      M  E  H  K  E  V  V  L  L  L  L  F  L  K  S  G  Q  G
CAAAATGGAACATAAGGAAGTGGTTCTTCTACTTCTTTTATTTCTGAAATCAGGTCAAGG
    70        80        90       100       110       120

>Glu plg
      E  P  L  D  D  Y  V  N  T  Q  G  A  S  L  F  S  V  T  K  K
AGAGCCTCTGGATGACTATGTGAATACCCAGGGGGCTTCACTGTTCAGTGTCACTAAGAA
    130       140       150       160       170       180

Q  L  G  A  G  S  I  E  E  C  A  A  K  C  E  E  D  E  E  F
GCAGCTGGGAGCAGGAAGTATAGAAGAATGTGCAGCAAAATGTGAGGAGGACGAAGAATT
    190       200       210       220       230       240

T  C  R  A  F  Q  Y  H  S  K  E  Q  Q  C  V  I  M  A  E  N
CACCTGCAGGGCATTCCAATATCACAGTAAAGAGCAACAATGTGTGATAATGGCTGAAAA
    250       260       270       280       290       300

R  K  S  S  I  I  I  R  M  R  D  V  V  L  F  E  K  K  V  Y
CAGGAAGTCCTCCATAATCATTAGGATGAGAGATGTAGTTTTATTTGAAAAGAAAGTGTA
    310       320       330       340       350       360

L  S  E  C  K  T  G  N  G  K  N  Y  R  G  T  M  S  K  T  K
TCTCTCAGAGTGCAAGACTGGGAATGGAAAGAACTACAGAGGGACGATGTCCAAAACAAA
    370       380       390       400       410       420

N  G  I  T  C  Q  K  W  S  S  T  S  P  H  R  P  R  F  S  P
AAATGGCATCACCTGTCAAAAATGGAGTTCCACTTCTCCCCACAGACCTAGATTCTCACC
    430       440       450       460       470       480

A  T  H  P  S  E  G  L  E  E  N  Y  C  R  N  P  D  N  D  P
TGCTACACACCCCTCAGAGGGACTGGAGGAGAACTACTGCAGGAATCCAGACAACGATCC
    490       500       510       520       530       540

Q  G  P  W  C  Y  T  T  D  P  E  K  R  Y  D  Y  C  D  I  L
GCAGGGGCCCTGGTGCTATACTACTGATCCAGAAAAGAGATATGACTACTGCGACATTCT
    550       560       570       580       590       600

E  C  E  E  E  C  M  H  C  S  G  E  N  Y  D  G  K  I  S  K
TGAGTGTGAAGAGGAATGTATGCATTGCAGTGGAGAAAACTATGACGGCAAAATTTCCAA
    610       620       630       640       650       660
```

FIG. 2B

```
        T  M  S  G  L  E  C  Q  A  W  D  S  Q  S  P  H  A  H  G  Y
      GACCATGTCTGGACTGGAATGCCAGGCCTGGGACTCTCAGAGCCCACACGCTCATGGATA
          670       680       690       700       710       720

I  P  S  K  F  P  N  K  N  L  K  K  N  Y  C  R  N  P  D  R
      CATTCCTTCCAAATTTCCAAACAAGAACCTGAAGAAGAATTACTGTCGTAACCCCGATAG
          730       740       750       760       770       780

E  L  R  P  W  C  F  T  T  D  P  N  K  R  W  E  L  C  D  I
      GGAGCTGCGGCCTTGGTGTTTCACCACCGACCCCAACAAGCGCTGGGAACTTTGCGACAT
          790       800       810       820       830       840

P  R  C  T  T  P  P  P  S  S  G  P  T  Y  Q  C  L  K  G  T
      CCCCCGCTGCACAACACCTCCACCATCTTCTGGTCCCACCTACCAGTGTCTGAAGGGAAC
          850       860       870       880       890       900

G  E  N  Y  R  G  N  V  A  V  T  V  S  G  H  T  C  Q  H  W
      AGGTGAAAACTATCGCGGGAATGTGGCTGTTACCGTGTCCGGGCACACCTGTCAGCACTG
          910       920       930       940       950       960

S  A  Q  T  P  H  T  H  N  R  T  P  E  N  F  P  C  K  N  L
      GAGTGCACAGACCCCTCACACACATAACAGGACACCAGAAAACTTTCCCTGCAAAAATTT
          970       980       990      1000      1010      1020

D  E  N  Y  C  R  N  P  D  G  K  R  A  P  W  C  H  T  T  N
      GGATGAAAACTACTGCCGCAATCCTGACGGAAAAAGGGCCCCCATGGTGCCATACAACCAA
         1030      1040      1050      1060      1070      1080

S  Q  V  R  W  E  Y  C  K  I  P  S  C  D  S  S  P  V  S  T
      CAGCCAAGTGCGGTGGGAGTACTGTAAGATACCGTCCTGTGACTCCTCCCCAGTATCCAC
         1090      1100      1110      1120      1130      1140

E  Q  L  A  P  T  A  P  P  E  L  T  P  V  V  Q  D  C  Y  H
      GGAACAATTGGCTCCCACAGCACCACCTGAGCTAACCCCTGTGGTCCAGGACTGCTACCA
         1150      1160      1170      1180      1190      1200

G  D  G  Q  S  Y  R  G  T  S  S  T  T  T  T  G  K  K  C  Q
      TGGTGATGGACAGAGCTACCGAGGCACATCCTCCACCACCACCACAGGAAAGAAGTGTCA
         1210      1220      1230      1240      1250      1260

S  W  S  S  M  T  P  H  R  H  Q  K  T  P  E  N  Y  P  N  A
      GTCTTGGTCATCTATGACACCACACCGGCACCAGAAGACCCCAGAAAACTACCCAAATGC
         1270      1280      1290      1300      1310      1320

G  L  T  M  N  Y  C  R  N  P  D  A  D  K  G  P  W  C  F  T
      TGGCCTGACAATGAACTACTGCAGGAATCCAGATGCCGATAAAGGCCCCTGGTGTTTTAC
         1330      1340      1350      1360      1370      1380
```

FIG. 2C

```
        T   D   P   S   V   R   W   E   Y   C   N   L   K   K   C   S   G   T   E   A
      CACAGACCCCAGCGTCAGGTGGGAGTACTGCAACCTGAAAAAATGCTCAGGAACAGAAGC
         1390      1400      1410      1420      1430      1440

S   V   V   A   P   P   P   V   V   L   L   P   D   V   E   T   P   S   E   E
      GAGTGTTGTAGCACCTCCGCCTGTTGTCCTGCTTCCAGATGTAGAGACTCCTTCCGAAGA
         1450      1460      1470      1480      1490      1500

D   C   M   F   G   N   G   K   G   Y   R   G   K   R   A   T   T   V   T   G
      AGACTGTATGTTTGGGAATGGGAAAGGATACCGAGGCAAGAGGGCGACCACTGTTACTGG
         1510      1520      1530      1540      1550      1560

T   P   C   Q   D   W   A   A   Q   E   P   H   R   H   S   I   F   T   P   E
      GACGCCATGCCAGGACTGGGCTGCCCAGGAGCCCCATAGACACAGCATTTTCACTCCAGA
         1570      1580      1590      1600      1610      1620

T   N   P   R   A   G   L   E   K   N   Y   C   R   N   P   D   G   D   V   G
      GACAAATCCACGGGCGGGTCTGGAAAAAAATTACTGCCGTAACCCTGATGGTGATGTAGG
         1630      1640      1650      1660      1670      1680

G   P   W   C   Y   T   T   N   P   R   K   L   Y   D   Y   C   D   V   P   Q
      TGGTCCCTGGTGCTACACGACAAATCCAAGAAAACTTTACGACTACTGTGATGTCCCTCA
         1690      1700      1710      1720      1730      1740

C   A   A   P   S   F   D   C   G   K   P   Q   V   E   P   K   K   C   P   G
      GTGTGCGGCCCCTTCATTTGATTGTGGGAAGCCTCAAGTGGAGCCGAAGAAATGTCCTGG
         1750      1760      1770      1780      1790      1800

R   V   V   G   G   C   V   A   H   P   H   S   W   P   W   Q   V   S   L   R
      AAGGGTTGTAGGGGGGTGTGTGGCCCACCCACATTCCTGGCCCTGGCAAGTCAGTCTTAG
         1810      1820      1830      1840      1850      1860

T   R   F   G   M   H   F   C   G   G   T   L   I   S   P   E   W   V   L   T
      AACAAGGTTTGGAATGCACTTCTGTGGAGGCACCTTGATATCCCCAGAGTGGGTGTTGAC
         1870      1880      1890      1900      1910      1920

A   A   H   C   L   E   K   S   P   R   P   S   S   Y   K   V   I   L   G   A
      TGCTGCCCACTGCTTGGAGAAGTCCCCAAGGCCTTCATCCTACAAGGTCATCCTGGGTGC
         1930      1940      1950      1960      1970      1980

H   Q   E   V   N   L   E   P   H   G   Q   E   I   E   V   S   R   L   F   L
      ACACCAAGAAGTGAATCTCGAACCGCATGGTCAGGAAATAGAAGTGTCTAGGCTGTTCTT
         1990      2000      2010      2020      2030      2040

E   P   T   R   K   D   I   A   L   L   K   L   S   S   P   A   V   I   T   D
      GGAGCCCACACGAAAAGATATTGCCTTGCTAAAGCTAAGCAGTCCTGCCGTCATCACTGA
         2050      2060      2070      2080      2090      2100
```

FIG. 2D

```
      K   V   I   P   A   C   L   P   S   P   N   Y   V   V   A   D   R   T   E   C
    CAAAGTAATCCCAGCTTGTCTGCCATCCCCAAATTATGTGGTCGCTGACCGGACCGAATG
         2110       2120      2130       2140      2150      2160

F   I   T   G   W   G   E   T   Q   G   T   F   G   A   G   L   L   K   E   A
    TTTCATCACTGGCTGGGGAGAAACCCAAGGTACTTTTGGAGCTGGCCTTCTCAAGGAAGC
         2170       2180      2190       2200      2210      2220

Q   L   P   V   I   E   N   K   V   C   N   R   Y   E   F   L   N   G   R   V
    CCAGCTCCCTGTGATTGAGAATAAAGTGTGCAATCGCTATGAGTTTCTGAATGGAAGAGT
         2230       2240      2250       2260      2270      2280

Q   S   T   E   L   C   A   G   H   L   A   G   G   T   D   S   C   Q   G   D
    CCAATCCACCGAACTCTGTGCTGGGCATTTGGCCGGAGGCACTGACAGTTGCCAGGGTGA
         2290       2300      2310       2320      2330      2340

S   G   G   P   L   V   C   F   E   K   D   K   Y   I   L   Q   G   V   T   S
    CAGTGGAGGTCCTCTGGTTTGCTTCGAGAAGGACAAATACATTTTACAAGGAGTCACTTC
         2350       2360      2370       2380      2390      2400

W   G   L   G   C   A   R   P   N   K   P   G   V   Y   V   R   V   S   R   F
    TTGGGGTCTTGGCTGTGCACGCCCCAATAAGCCTGGTGTCTATGTTCGTGTTTCAAGGTT
         2410       2420      2430       2440      2450      2460

V   T   W   I   E   G   V   M   R   N   N
    TGTTACTTGGATTGAGGGAGTGATGAGAAATAATTAATTGGACGGGAGACAGAGTGACGC
         2470       2480      2490       2500      2510      2520

SphI
    ACTGACTCACCTAGAGGCTGGAACGTGGGTAGGGATTTAGCATG^CTGGAAATAACTGGCA
         2530       2540      2550       2560      2570      2580

GTAATCAAACGAAGACACTGTCCCCAGCTACCAGCTACGCCAAACCTCGGCATTTTTTGT
         2590       2600      2610       2620      2630      2640

GTTATTTTCTGACTGCTGGATTCTGTAGTAAGGTGACATAGCTATGACATTTGTTAAAAA
         2650       2660      2670       2680      2690      2700

TAAACTCTGTACTTAACTTTGATTTGAGTAAATTTTGGTTTTGGTCTTCAACA
         2710       2720      2730       2740      2750
```

FIG. 4A

CLEAVAGE SITE AMINO ACID SEQUENCES — Factor Xa series

```
       555 556 557 558 559 560 561 562 563 564 565 566
WT     Pro Lys Lys Cys Pro Gly Arg Val Val Gly Gly Cys
       CCG AAG AAA TGT CCT GGA AGG GTT GTG GGG GGG TGT
```

FACTOR Xa CLEAVABLE ANALOGUES

```
X1     Pro Lys Lys Cys Ile Glu Gly Arg Val Val Gly Gly Cys
       CCG AAG AAA TGT ATC GAG GGA AGG GTT GTG GGG GGG TGT

X2     Pro Lys Lys Cys Gly Ile Glu Gly Arg Val Val Gly Gly Cys
       CCG AAG AAA TGT GGC ATC GAG GGA AGG GTT GTG GGG GGG TGT

X3     Pro Lys Lys Cys Gly Ala Ile Glu Gly Arg Val Val Gly Gly Cys
       CCG AAG AAA TGT GGT GCA ATA GAG GGA AGG GTT GTG GGG GGG TGT

X5     Pro Lys Lys Cys Gly Tyr Ile Asp Gly Arg Val Val Gly Gly Cys
```

FIG. 4B

CCG AAG AAA TGT GGT TAC ATA GAC GGA AGG GTT GTG GGG GGG TGT

Pro Lys Lys Cys Gly Tyr Ile Asp Gly Arg Ile Val Gly Gly Cys
CCG AAG AAA TGT GGT TAC ATA GAC GGA AGG ATT GTG GGG GGG TGT x6

FIG. 5A

CLEAVAGE SITE AMINO ACID SEQUENCES — Thrombin series

WILD-TYPE PLASMINOGEN

```
      553 554 555 556 557 558 559 560 561 562 563 564 565 566
WT    Val Glu Pro Lys Lys Cys Pro Gly Arg Val Val Gly Gly Cys
      GTG GAG CCG AAG AAA TGT CCT GGA AGG GTT GTG GGG GGG TGT
```

THROMBIN CLEAVABLE ANALOGUES

```
      553 554 555 556 557 558 559 560 561 562 563 564 565 566
T1    Val Glu Pro Lys Lys Cys Gly Pro Arg Val Val Gly Gly Cys
      GTG GAG CCG AAG AAA TGT GGT CCT AGG GTT GTG GGG GGG TGT

T2    Val Glu Pro Lys Lys Cys Gly Gly Pro Arg Val Val Gly Gly Cys
      GTG GAG CCG AAG AAA TGT GGT GGT CCA AGG GTT GTG GGG GGG TGT

T6    Leu Glu Pro Glu Leu Cys Gly Val Val Pro Arg Gly Val Gly Gly Cys
      CTG GAG CCG GAG CTA TGT GGA GTT GTG CCT AGG GGA GTG GGG GGG TGT

T7    Leu Glu Pro Gln Leu Cys Gly Val Val Pro Arg Gly Val Gly Gly Cys
      CTG GAG CCG CAA CTA TGT GGA GTT GTG CCT AGG GGA GTG GGG GGG TGT

T8    Val Glu Pro Lys Lys Cys Val Glu Leu Gln Gly Val Val Pro Arg Gly
      GTG GAG CCG AAG AAA TGT GTA GAA CTA CAA GGA GTA GTG CCT AGG GGA

Val Gly Gly Cys
      GTG GGG GGG TGT

T13   Val Glu Pro Lys Lys Cys Val Val Pro Arg Val Val Gly Gly Cys
```

FIG. 5B

```
          GTG GAG CCG AAG AAA TGT GTT GTA CCT AGG GTT GTG GGG GGG TGT

T14       Val Glu Pro Lys Lys Cys Gly Tyr Pro Arg Val Val Gly Gly Cys
          GTG GAG CCG AAG AAA TGT GGA TAC CCT AGG GTT GTG GGG GGG TGT

T17       Val Glu Pro Lys Lys Cys Pro Ser Gly Arg Val Val Gly Gly Cys
          GTG GAG CCG AAG AAA TGT CCT AGT GGA AGG GTT GTG GGG GGG TGT

T19       Val Glu Pro Lys Lys Cys Val Glu Leu Gln Gly Val Val Pro Arg
          GTG GAG CCG AAG AAA TGT GTA GAA TTG CAG GGA GTA GTC CCA AGG

Val Val Gly Gly Cys
          GTT GTG GGG GGG TGT

T20       Val Glu Pro Lys Lys Cys Val Glu Leu Gln Gly Val Val Pro Arg
          GTG GAG CCG AAG AAA TGT GTA GAA TTG CAG GGA GTA GTC CCA AGG

Gly Gly Cys
          GGG GGG TGT

T21       Leu Glu Pro Glu Leu Cys Gly Val Val Pro Arg Val Val Gly Gly Cys
          CTG GAG CCG GAG CTA TGT GGA GTT GTG CCT AGG GTA GTG GGG GGG TGT

T22       Leu Glu Pro Gln Leu Cys Gly Val Val Pro Arg Val Val Gly Gly Cys
          CTG GAG CCG CAA CTA TGT GGA GTT GTG CCT AGG GTA GTG GGG GGG TGT
```

FIBRIN AGAR CLOT LYSIS GEL

Wells 1 and 2 = X2 plus Factor Xa
Wells 3 and 4 = X2 minus Factor Xa

Wells 5 and 6 = T2 plus thrombin
Wells 7 and 8 = T2 minus thrombin

Wells 2, 4, 6 and 8 were pretreated with hirudin before loading the samples

CLEAVAGE ANALYSIS ON SDS PAGE

Lane 1   X2 cleaved with Factor Xa
Lane 2   X2 minus Factor Xa
Lane 3   T2 cleaved with thrombin
Lane 4   T2 minus thrombin
Lane 5   Protein markers

ACTIVATABLE FIBRINOLYTIC AND ANTI-THROMBOTIC PROTEINS

This invention relates to proteinaceous compounds which can be activated to have fibrinolytic activity or to inhibit blood clot formation. It also relates to nucleic acid (DNA and RNA) coding for all or part of such compounds. In preferred embodiments, the invention relates to plasminogen analogues, their preparation, pharmaceutical compositions containing them and their use in the treatment of thrombotic disease.

Plasminogen is a key component of the fibrinolytic system which is the natural counterpart to the clotting system in the blood. In the process of blood coagulation, a cascade of enzyme activities are involved in generating a fibrin network which forms the framework of a clot, or thrombus. Degradation of the fibrin network (fibrinolysis) is accomplished by the action of the enzyme plasmin. Plasminogen is the inactive precursor of plasmin and conversion of plasminogen to plasmin is accomplished by cleavage of the peptide bond between arginine 561 and valine 562 of plasminogen. Under physiological conditions this cleavage is catalysed by tissue-type plasminogen activator (tPA) or by urokinase-type plasminogen activator (uPA).

If the balance between the clotting and fibrinolytic systems becomes locally disturbed, intravascular clots may form at inappropriate locations leading to conditions such as coronary thrombosis and myocardial infarction, deep vein thrombosis, stroke, peripheral arterial occlusion and embolism. In such cases, the administration of fibrinolytic agents has been shown to be a beneficial therapy for the promotion of clot dissolution.

Fibrinolytic therapy has become relatively widespread with the availability of a number of plasminogen activators such as tPA, uPA, streptokinase and the anisoylated plasminogen streptokinase activator complex, APSAC. Each of these agents has been shown to promote clot lysis, but all have deficiencies in their activity profile which makes them less than ideal as therapeutic agents for the treatment of thrombosis (reviewed by Marder and Sherry, *New England Journal of Medicine* 1989, 318: 1513–1520). One of the major problems with tPA for the treatment of acute myocardial infarction or other thrombotic disorders is that it is rapidly cleared from the circulation with a plasma half-life in man of around 5 minutes (Bounameaux et al in: "Contemporary Issues in Haemostasis and Thrombosis" vol 1 p5–91, 1985. Collen et al eds, Churchill Livingstone). This results in the need to administer tPA by infusion in large doses. The treatment is therefore expensive and is delayed as the patient has to be hospitalised before treatment can commence. Urokinase, in either the single chain form (scuPA) or the two chain form (tcuPA), has a similar rapid plasma clearance and also requires administration by continuous infusion.

A major problem shared by all of these agents is that at clinically useful doses, they are not thrombus specific as they activate plasminogen in the general circulation. The principal consequence of this is that proteins such as fibrinogen involved in blood clotting are destroyed and dangerous bleeding can occur. This also occurs with tPA despite the fact that, at physiological concentrations, it binds to fibrin and shows fibrin selective plasminogen activation.

Another important shortcoming in the performance of existing plasminogen activators is that re-occlusion of the reperfused blood vessel commonly occurs after cessation of administration of the thrombolytic agent. This is thought to be due to the persistence of thrombogenic material at the site of thrombus dissolution.

An alternative approach to enhancing fibrinolysis has now been devised which is based on the use of molecules activatable to have fibrinolytic activity or to inhibt clot formation. The activation (which may involve cleavage) can be catalysed by one or more endogenous enzymes involved in blood clotting. An advantage of this approach is that thrombus selectivity of fibrinolytic or inhibition of clot formation activity is achieved by way of the thrombus-specific localisation of the activating enzymes.

According to a first aspect of the present invention, there is provided a proteinaceous compound which is activatable, by an enzyme involved in blood clotting, to have fibrinolytic activity or to inhibit clot formation.

Proteinaceous compounds in accordance with the first aspect of the invention, are therefore activatable in at least one of two ways. First, a compound may be activated to have fibrinolytic activity. Secondly, a compound may be activated to inhibit clot formation. Conceivably, a compound may be activatable to have both functions. Activation is most conveniently achieved by cleavage, in many cases.

Preferably the compound, when activated, has substantially the same qualitative activity as a natural mammalian fibrinolytic agent and/or a mammalian inhibitor of clot formation. In quantitative terms, while it is preferred that the activity be as good as, if not better than, the natural compound, the benefits of the invention may still be had if the activity is not as good. It will be understood that preferred compounds of the invention may therefore have the same qualitative activity as a natural precursor of a natural mammalian fibrinolytic agent and/or a mammalian inhibitor of clot formation. Again, in quantitative terms, the facility with which the precursor can be activated is preferably, but need not necessarily be, as good as the natural compound.

A natural proteinaceous compound which is activatable to have fibrinolytic activity is plasminogen, which is cleaved to form plasmin. Plasminogen analogues form a preferred group of compounds of this invention.

Analysis of the wild-type plasminogen molecule has revealed that it is a glycoprotein composed of a serine protease domain, five kringle domains and an N-terminal sequence of 78 amino acids which may be removed by plasmin cleavage. Cleavage by plasmin involves hydrolysis of the Arg(68)-Met(69), Lys(77)-Lys(78) or Lys(78)-Val(79) bonds to create forms of plasminogen with an N-terminal methionine, lysine or valine residue, all of which are commonly designated as lys-plasminogen. Intact plasminogen is referred to as glu-plasminogen because it has an N-terminal glutamic acid residue. Glycosylation occurs on residues Asn(289) and Thr(346) but the extent and composition are variable, leading to the presence of a number of different molecular weight forms of plasminogen in the plasma. The serine protease domain can be recognised by its homology with other serine proteases and on activation to plasmin is the catalytically active domain involved in fibrin degradation. The five kringle domains are homologous to those in other plasma proteins such as tPA and prothrombin and are involved in fibrin binding and thus localisation of plasminogen and plasmin to thrombi. Plasminogen is a zymogen which normally circulates in the blood as a single polypeptide chain and is converted to the two-chain enzyme plasmin by cleavage of a peptide bond between amino acids 561 (arg) and 562 (val). This cleavage is catalysed specifically by plasminogen activators such as tPA and uPA. This is reviewed in: Castellino, F. J., 1984, *Seminars in Thrombosis and Haemostasis* 10; 18–23. In this specification, plasminogen is numbered according to the protein sequencing studies of Sottrup-Jensen et al (in: Atlas of Protein Sequence and Structure (Dayhoff, M. O., ed.) 5 suppl. 3, p.95 (1978)) which indicated that plasminogen was a 790 amino acid protein and that the site of cleavage was the Arg(560)-Val (561) peptide bond. However, a suitable plasminogen cDNA useful in this embodiment of the invention and that isolated by Forsgren et al (*FEBS Letters* 213 254–260 (1987)) code for a 791 residue protein with an extra Ile at position 65. In this specification, the numbering of the amino acids in plasminogen corresponds to that of the cDNA used. There may be polymorphism in the structure of plasminogen and there may be forms of plasminogen in which the numbering of the cleavage site differs but it is intended that such variants be included in the embodiment.

Therefore the term "plasminogen analogue", as used in this specification, means a molecule differing from wild type plasminogen and having the ability to be cleaved or otherwise acted on to form a molecule having plasmin activity.

The plasma half-life of glu-plasminogen has been determined to be 2.2 days and that of lys-plasminogen to be 0.8 days (Claeys, H. and Vermylen, J. 1974. *Biochim. Biophys. Acta* 342: 351–359; Wallen, P. and Wiman, B. in: "Proteases and Biological Control", 291–303. Reich, E. et al. eds, Cold Spring Harbor Laboratory).

Plasminogen analogues within the scope of this embodiment of the invention retain the fibrin binding activity of wild type plasminogen to an adequate degree but have altered activation characteristics; preferred plasminogen analogues have a plasma half life which is at least that of wild type plasminogen, but this property is not essential.

The blood coagulation mechanism comprises a series of enzyme reactions which culminate in the production of insoluble fibrin, which forms the mesh-like protein framework of blood clots. Thrombin is the enzyme responsible for the conversion of soluble fibrinogen to fibrin. Conversion of prothrombin, the inactive precursor of thrombin, to thrombin is catalysed by activated Factor X (Factor Xa). (Thrombin is also known as Factor IIa, and prothrombin as Factor II.)

Factor Xa is generated from Factor X extrinsically or intrinsically. In the extrinsic route, Factor VII is activated to Factor VIIa, which generates Factor Xa from Factor X. In the intrinsic route, the activation of Factor X to Factor Xa is catalysed by Factor IXa. Factor IXa is generated from Factor IX by the action of Factor XIa, which in turn is generated by the action of Factor XIIa on Factor XI. Factor XIIa is generated from Factor XII by the action of Kallikrein. Factors VIIIa and Va are thought to act as cofactors in the activation of Factors X and II, respectively.

Fibrin, as first formed from fibrinogen, is in the loose form. Loose fibrin is converted to tight fibrin by the action of Factor XIIIa, which crosslinks fibrin molecules.

Activated protein C is an anticoagulant serine protease generated in the area of clot formation by the action of thrombin, in combination with thrombomodulin, on protein C. Activated protein C regulates clot formation by cleaving and inactivating the pro-coagulant cofactors Va and VIIIa.

The term "enzyme involved in blood clotting" as used in this specification therefore includes kallikrein Factors XIIa, XIa, IXa, VIIa, Xa and thrombin (Factor IIa), which are directly involved in the formation of fibrin and activated protein C, which is involved in the control of blood clotting. The most preferred enzymes are Factor Xa and thrombin because they are most immediately involved with fibrin formation.

Generation and activity of at least Factor Xa and thrombin is tightly regulated to ensure that thrombus generation is restricted to the site of the thrombogenic stimulus. This localisation is achieved by the combined operation of at least two control mechanisms: the blood clotting enzymes function as complexes intimately associated with the phospholipid cellular membranes of platelets and endothelial cells at the site of vascular injury (Mann, K. G., 1984, in: "Progress in Hemostasis and Thrombosis", 1–24, ed Spaet, T. H. Grune and Stratton); and, free thrombin or Factor Xa released from the thrombus site into the circulation is rapidly inactivated by the action of proteinase inhibitors such as antithrombin III.

Thus, the activity of the penultimate (Factor Xa) and the final (thrombin) enzymes in the clotting cascade are particularly well localised to the site of thrombus generation and for this reason are preferred.

Thrombin has been found to remain associated with thrombi and to bind non-covalently to fibrin. On digestion of thrombi with plasmin, active thrombin is liberated and is thought to contribute to the reformation of thrombi and the re-occlusion of vessels which commonly occurs following thrombolytic treatment with plasminogen activators (Bloom A. L., 1962, *Br. J. Haematol*, 82, 129; Francis et al, 1983, *J. Lab. Clin. Med.*, 102, 220; Mirshahi et al, 1989, *Blood* 74, 1025).

For these reasons, it is preferred in certain embodiments of the invention to modify plasminogen or another potentially activatable proteinaceous compound to make it activatable by thrombin or Factor Xa thereby to create a preferred class of thrombus-selective, fibrinolytic or clot formation inhibiting proteins. The most preferred plasminogen analogues retain the favourable property of the parent plasminogen molecule of possessing a long plasma half-life and exhibit thrombus selectivity by a combination of two mechanisms, namely, fibrin binding via the kringle domains and the novel property of being converted to plasmin at the site of new thrombus formation by the action of one of the enzymes involved in generation of the thrombus and preferably localised there.

Factor Xa (E.C.3.4.21.6) is a serine protease which converts human prothrombin to thrombin by specific cleavage of the Arg(273)-Thr(274) and Arg(322)-Ile(323) peptide bonds (Mann et al 1981, *Methods in Enzymology* 80 286–302). In human prothrombin, the Arg(273)-Thr(274) site is preceded by the tripeptide Ile-Glu-Gly and the Arg (322)-Ile(323) site is preceded by the tripeptide Ile-Asp-Gly. The structure required for recognition by Factor Xa appears to be determined by the local amino acid sequence preceding the cleavage site (Magnusson et al, 1975, in: "Proteases and Biological Control", 123–149, eds., Reich et al, Cold Spring Harbor Laboratory, New York). Specificity for the Ile-Glu-Gly-Arg and Ile-Asp-Gly-Arg sequence is not absolute as Factor Xa has been found to cleave other proteins, for example Factor VIII at positions 336, 372, 1689 and 1721, where the preceding amino acid sequence differs significantly from this format (Eaton et al, 1986 *Biochemistry* 25 505–512). As the principal natural substrate for Factor Xa is prothrombin, preferred recognition sequences are those in which arginine and glycine occupy the P1 and P2 positions, respectively, an acidic residue (aspartic or glutamic acid) occupies the P3 position and isoleucine or another small hydrophobic residue (such as alanine, valine, leucine or methionine) occupies the P4 position. However, as Factor Xa can cleave sequences which differ from this format, other sequences cleavable by Factor Xa may be used in the invention, as can other sequences cleavable by other enzymes of the clotting cascade.

Conversion of plasminogen to plasmin by tPA and uPA involves cleavage of the peptide bond between arginine 561 and valine 562 to produce a disulphide linked, two chain protein with an amino-terminal valine on the light (protease domain) chain and a carboxy-terminal arginine on the heavy chain. Plasminogen is not cleaved and activated to any significant extent by thrombin or Factor Xa and in order to make plasminogen analogues which are cleavable by these preferred enzymes, the cleavage site Pro(559), Gly(560), Arg(561), Val(562) recognised by tPA and uPA has to be altered. To make plasminogen analogues which are cleaved by, for example, Factor Xa, an amino acid sequence cleavable by Factor Xa may be substituted into the plasminogen molecule. The sequence Ile-Glu-Gly-Arg which is at one of the sites in prothrombin cleaved by Factor Xa may be such a sequence. Other possibilities would be sequences or mimics of sequences cleaved by Factor Xa in other proteins or peptides. A plasminogen analogue in which Pro(558) is removed and replaced by Ile-Glu, may have the Arg(561)-Val(562) (wild-type plasminogen numbering) peptide bond cleaved by Factor Xa to produce a disulphide-linked, two-chain plasmin analogue, with an amino-terminal valine on the light (protease domain) chain and a carboxy-terminal arginine on the heavy chain. DNA coding for the Ile-Glu-Gly-Arg sequence as the carboxy-terminal part of a cleavable linker as a protein production aid is disclosed in UK Patent Application GB-A-2160206 but the use of an Ile-Glu-Gly-Arg sequence to allow an altered activation process for a zymogen is not disclosed in that specification.

Cleavage and activation of plasminogen variants or other potentially activatable proteinaceous compounds by an enzyme of the clotting cascade such as thrombin or Factor Xa can be measured in a number of ways, for example by SDS-PAGE analysis, and in the case of plasminogen variants by assaying for the formation of plasmin using the S2251 chromogenic assay or a fibrin gel lysis assay.

Thrombin (E.C. 3.4.21.5) is a serine protease which catalyses the proteolysis of a number of proteins including fibrinogen (A alpha and B beta chains), Factor XIII, Factor V, Factor VII, Factor VIII, protein C and antithrombin III. The structure required for recognition by thrombin appears to be partially determined by the local amino acid sequence around the cleavage site but is also determined to a variable extent by sequence(s) remote from the cleavage site. For example, in the fibrinogen A alpha chain, residues P2 (Val), P9 (Phe) and P10 (Asp) are crucial for α-thrombin-catalysed cleavage at the Arg(16)-Gly(17) peptide bond (Ni, F. et al 1989, *Biochemistry* 28 3082–3094). Comparative studies of several proteins and peptides which are cleaved by thrombin has led to the proposal that optimum cleavage sites for α-thrombin may have the structure of (i) P4-P3-Pro-Arg-P1'-P2' where each of P3 and P4 is independently a hydrophobic amino acid (such as valine) and each of P1' and P2' is independently a non-acidic amino acid such as a hydrophobic amino acid like valine, or (ii) P2-Arg-P1' where P2 or P1' is glycine (Chang, J. 1985, *Eur. J. Biochem.* 151 217–224). There are, however, exceptions to these general structures which are cleaved by thrombin and which may be used in the invention.

To produce a plasminogen analogue which could be cleaved and activated by thrombin, a site recognised and cleaved by thrombin may be substituted into the plasminogen molecule at an appropriate location. An amino acid sequence such as that cleaved by thrombin in the fibrinogen A alpha chain may be used. Other possible sequences would include those involved in the cleavage by thrombin of fibrinogen B beta, Factor XIII, Factor V, Factor VII, Factor VIII, protein C, anti-thrombin III and other proteins whose cleavage is catalysed by thrombin. An example of a thrombin cleavable analogue of plasminogen may be one in which the sequence Pro(559), Gly(560) is changed to Gly(559), Pro(560) to produce a sequence Gly(559)-Pro(560)-Arg(561)-Val(562) which is identical to that found at positions 17–20 in fibrinogen A alpha. This is not the principal thrombin cleavage site in fibrinogen A alpha but thrombin can cleave the Arg(19)-Val(20) peptide bond.

Such subtle changes are important if the important features of full activity and stability are to be retained in the mutant derivative, as is preferred.

In a preferred embodiment the invention relates to plasminogen analogues with single or multiple amino acid substitutions, additions or deletions between residues Pro (555) and Cys(566) inclusive. Such plasminogen analogues are cleaved by thrombin, Factor Xa or other enzymes involved in blood clotting to produce plasmin analogues with fibrinolytic activity.

Plasminogen analogues in accordance with the preferred embodiment of the invention may contain other modifications (as compared to wild-type glu-plasminogen) which may be one or more additions, deletions or substitutions. An example of such a modification would be the addition, removal, substitution or alteration of one or more kringle domains to enhance fibrin binding activity.

An example of a modification involving deletion would be lys-plasminogen variants of plasminogen analogues in which the amino terminal 68, 77 or 78 amino acids have been deleted. Such variants may have enhanced fibrin binding activity as has been observed for lys-plasminogen compared to wild-type glu-plasminogen (Bok, R. A. and Mangel, W. F. 1985, *Biochemistry* 24 3279–3286).

The plasmin inhibitor alpha-2 antiplasmin is present in the blood and becomes incorporated into the fibrin matrix of blood clots. The role of this inhibitor is to restrict plasmin activity in the clot and in the circulation. For the highly clot selective analogues of plasminogen of the present invention it may be advantageous to introduce a mutation in the serine protease domain that interferes with plasmin inhibitor binding. This mutation could be in a position analogous to that shown to prevent inhibitor binding to tissue plasminogen activator (Madison, E. L. et al 1989 *Nature* 339 721–724).

Other plurally-modified plasminogen analogues in accordance with the invention may include one or more modifications to prevent, reduce or alter glycosylation patterns. Plasminogen analogues incorporating such modifications may have a longer half-life, reduced plasma clearance and/or higher specific activity.

Other proteins may also be altered so that they are cleaved or otherwise activated, by enzymes involved in blood clotting, to be fibrinolytically active or to be inhibitory of clot formation. Single chain urokinase plasminogen activator (scuPA) is an example of a fibrinolytic protein and protein C is an example of an enzyme involved in inhibition of blood clotting which could be so activated.

scuPA is activated to two chain uPA (tcuPA) by plasmin cleavage of the Lys(158)-Ile(159) peptide bond. Thrombin inactivates scuPA by cleaving the Arg(156)-Phe(157) peptide bond. An analogue of scuPA could be constructed in which the amino acid sequence around the cleavage site was altered so that cleavage by thrombin, or another enzyme involved in blood clotting, would produce active tcuPA.

Protein C is cleaved to its activated form by the action of thrombin bound to thrombomodulin. A protein C analogue within the scope of this invention is modified so as to be cleavable by thrombin per se to form activated protein C.

Fusion proteins may be constructed to achieve selective release of fibrinolytic or anticoagulant proteins at the site of blood clotting. To achieve this, proteins involved in fibrinolysis or inhibition of coagulation are joined by a linker region which is cleavable by an enzyme involved in blood clotting. Examples of proteins which may be incorporated into such a cleavable protein include tPA, uPA, streptokinase, plasminogen, protein C, hirudin and antithrombin III. Fusion of such proteins to a protein with a favourable property not directly related to dissolution of blood clots (for example albumin, which has a long plasma half-life) may also be beneficial.

Preferred features of plasminogen analogues within the scope of the invention also apply, where appropriate, to other compounds of the invention, mutatis mutandis.

Compounds in accordance with the first aspect of the invention can be synthesised by any convenient route. According to a second aspect of the invention there is provided a process for the preparation of a proteinaceous compound as described above, the process comprising coupling successive amino acid residues together and/or ligating oligopeptides. Although proteins may in principle be synthesised wholly or partly by chemical means, the route of choice will be ribosomal translation, preferably in vivo, of a corresponding nucleic acid sequence. The protein may be glycosylated appropriately.

It is preferred to produce proteins in accordance with the invention by using recombinant DNA technology, particularly when they are analogues (whether by amino acid substitution, deletion or addition) of natural proteins. DNA encoding plasminogen or another natural protein may be from a cDNA or genomic clone or may be synthesised. Amino acid substitutions, additions or deletions are preferrably introduced by site-specific mutagenesis. Suitable DNA sequences encoding glu-plasminogen, lys-plasminogen and plasminogen analogues and other compounds within the scope of the invention may be obtained by procedures familiar to those having ordinary skill in genetic engineering. For several proteins, including for example tissue plasminogen activator, it is a routine procedure to obtain recombinant protein by inserting the coding sequence into an expression vector and transfecting the vector into a suitable host cell. A suitable host may be a bacterium such as *E. coli*, a eukaryotic microorganism such as yeast or a higher eukaryotic cell. Plasminogen, however, is unusually difficult to express and several unsuccessful attempts have been made at producing recombinant plasminogen in mammalian cells (Busby S. et al 1988, *Fibrinolysis* 2, Suppl. 1, 64; Whitefleet-Smith et al, 1989, *Arch. Bioc. Biop.* 271 390–399). It may be possible to express plasminogen in *E. coli* but the protein would be made in an insoluble form and would have to be renatured. Satisfactory renaturation would be difficult with current technology. Plasminogen has been expressed in insect cells using a baculovirus vector-infected cell system at levels of 0.7–1.0 µg/$10^6$ cells (measured 66 hours post infection) (Whitefleet-Smith et al, ibid) but this method does not generate a stable cell line producing plasminogen and any post-translational modifications, such as glycosylation, may not be authentic.

According to a third aspect of the invention, there is provided synthetic or recombinant nucleic acid coding for a proteinaceous compound as described above. The nucleic acid may be RNA or DNA. Preferred characteristics of this aspect of the invention are as for the first aspect.

According to a fourth aspect of the invention, there is provided a process for the preparation of nucleic acid in accordance with the third aspect, the process comprising coupling successive nucleotides together and/or ligating oligo- and/or poly-nucleotides.

Recombinant nucleic acid in accordance with the third aspect of the invention may be in the form of a vector, which may for example be a plasmid, cosmid or phage. The vector may be adapted to transfect or transform prokaryotic (for example bacterial) cells and/or eukaryotic (for example yeast or mammalian) cells. A vector will comprise a cloning site and usually at least one marker gene. An expression vector will have a promoter operatively linked to the sequence to be inserted in the cloning site, and, preferably, a sequence enabling the protein product to be secreted. Expression vectors and cloning vectors (which need not be capable of expression) are included in the scope of the invention.

Certain vectors are particularly useful in the present invention. According to a fifth aspect of the invention, there is provided a vector comprising a first nucleic acid sequence coding for a protein or embodying a cloning site, operatively linked to a second nucleic acid sequence containing a strong promoter and enhancer sequence derived from human cytomegalovirus, a third nucleic acid sequence encoding a polyadenylation sequence derived from SV40 and a fourth nucleic acid sequence coding for a selectable marker expressed from an SV40 promoter and having an additional SV40 polyadenylation signal at the 3' end of the selectable marker sequence.

It is to be understood that the term "vector" is used in this specification in a functional sense and is not to be construed as necessarily being limited to a single nucleic acid molecule. So, for example, the first, second and third sequences of the vector defined above may be embodied in a first nucleic acid molecule and the fourth sequence may be embodied in a second nucleic acid molecule.

The selectable marker may be any suitable marker. The gpt marker is appropriate.

Such a vector enables the expression of such proteins as plasminogen and plasminogen analogues (including glu-plasminogen and lys-plasminogen) which may otherwise be difficult to express.

This aspect of the invention provides the construction of a vector which is useful for the expression of foreign genes and cDNAs and for the production of heterologous proteins in mammalian cells. The particular embodiment exemplified is the construction of stable cell lines which are capable of expressing plasminogen and plasminogen analogues at high levels.

Using a vector, for example as described above, heterologous proteins, such as plasminogen and plasminogen analogues, are preferably expressed and secreted into the cell culture medium in a biologically active form without the need for any additional biological or chemical procedures. Suitable cells or cell lines to be transformed are preferably mammalian cells which grow in continuous culture and which can be transfected or otherwise transformed by standard techniques. Examples of suitable cells include Chinese hamster ovary (CHO) cells, mouse myeloma cell lines such as P3X63-Ag8.653, COS cells, HeLa cells, BHK cells, melanoma cell lines such as the Bowes cell line, mouse L cells, human hepatoma cell lines such as Hep G2, mouse fibroblasts and mouse NIH 3T3 cells.

It appears that the use of CHO cells as hosts for the expression of plasminogen and plasminogen analogues is particularly beneficial. According to a sixth aspect of the invention, there is therefore provided a chinese hamster ovary (CHO) cell transformed to express plasminogen or a plasminogen analogue.

CHO or other cells, such as yeast (for example *Saccharomyces cerevisiae*) or bacteria (for example *Escherichia* coli) may be preferred for the expression of other proteinaceous compounds of the invention. According to a seventh aspect of the invention, there is provided a cell or cell line transformed by nucleic acid and/or a vector as described above. Transformation may be achieved by any convenient method; electroporation is a method of choice.

Proteinaceous compounds of the present invention may be used within pharmaceutical compositions for the prevention or treatment of thrombosis or other conditions where it is desired to produce local fibrinolytic and/or anticoagulant activity. Such conditions include myocardial and cerebral infarction, arterial and venous thrombosis, thromboembolism, post-surgical adhesions, thrombophlebitis and diabetic vasculopathies.

According to an eighth aspect of the invention, there is provided a pharmaceutical composition comprising one or more compounds in accordance with the first aspect of the invention and a pharmaceutically or veterinarily acceptable carrier. Such a composition may be adapted for intravenous administration and may thus be sterile. Examples of compositions in accordance with the invention include preparations of sterile plasminogen analogue(s) in isotonic physiological saline and/or buffer. The composition may include a local anaesthetic to alleviate the pain of injection. Compounds of the invention may be supplied in unit dosage form, for example as a dry powder or water-free concentrate in a hermetically sealed container such as an ampoule or sachet indicating the quantity of protein. Where a compound is to be administered by infusion, it may be dispensed by means of an infusion bottle containing sterile water for injections or saline or a suitable buffer. Where it is to be administered by injections, it may be dispensed with an ampoule of water for injection, saline or a suitable buffer. The infusible or injectable composition may be made up by mixing the ingredients prior to administration. Where it is to be administered as a topical treatment, it may be dispensed in a suitable base.

The quantity of material to be administered will depend on the amount of fibrinolysis or inhibition of clotting required, the required speed of action, the seriousness of the thromboembolic position and the size of the clot. The precise dose to be administered will, because of the very nature of the condition which compounds of the invention are intended to treat, be determined by the physician. As a guideline, however, a patient being treated for a mature thrombus will generally receive a daily dose of a plasminogen analogue of from 0.01 to 10 mg/kg of body weight either by injection in for example up to 5 doses or by infusion.

The invention may be used in a method for the treatment or prophylaxis of thrombosis, comprising the administration of an effective non-toxic amount of a compound in accordance with the first aspect. According to a further aspect of the invention, there is therefore provided the use of a compound as described above in the preparation of a thrombolytic and/or anticoagulant agent.

The invention concerns especially the DNAs, the vectors, the transformed host strains, the plasminogen analogue proteins and the process for the preparation thereof as described in the examples.

The following figures and examples of the invention are offered by way of illustration, and not by way of limitation. Examples 1 to 3 describe the expression vector used for the expression of plasminogen and plasminogen variants from higher eukaryotic cells. Subsequent examples describe the expression of plasminogen and plasminogen variants and their properties. In the drawings referred to in the examples:

FIG. 1 shows the construction of pGWH;

FIG. 2 shows the nucleotide sequence of the glu-plasminogen cDNA and the predicted amino acid sequence;

FIG. 4 shows the cleavage site sequences of Factor Xa activated plasminogen analogues;

FIG. 5 shows the cleavage site sequences of thrombin activated plasminogen analogues;

Figure 7:
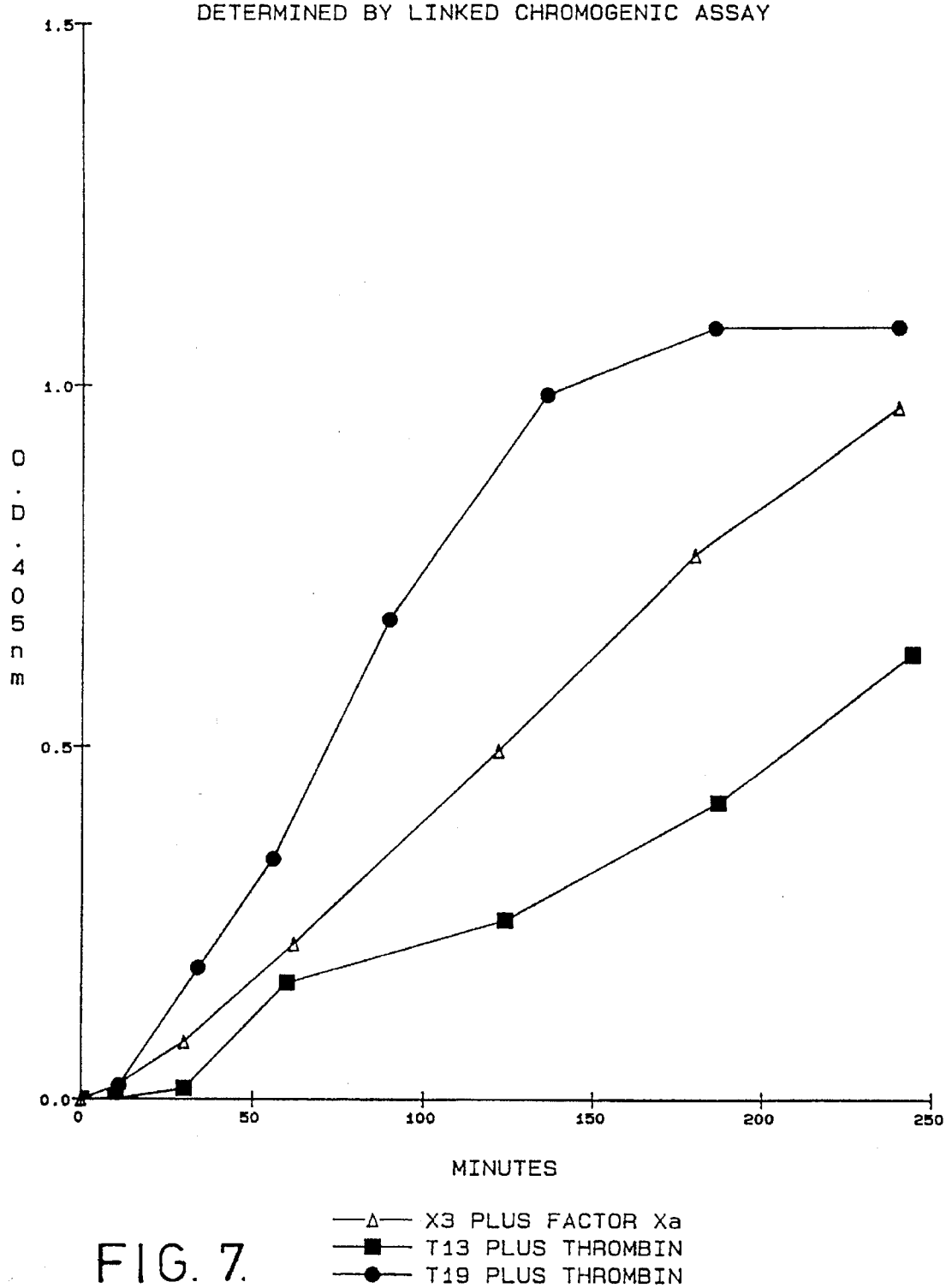
Figure 8:
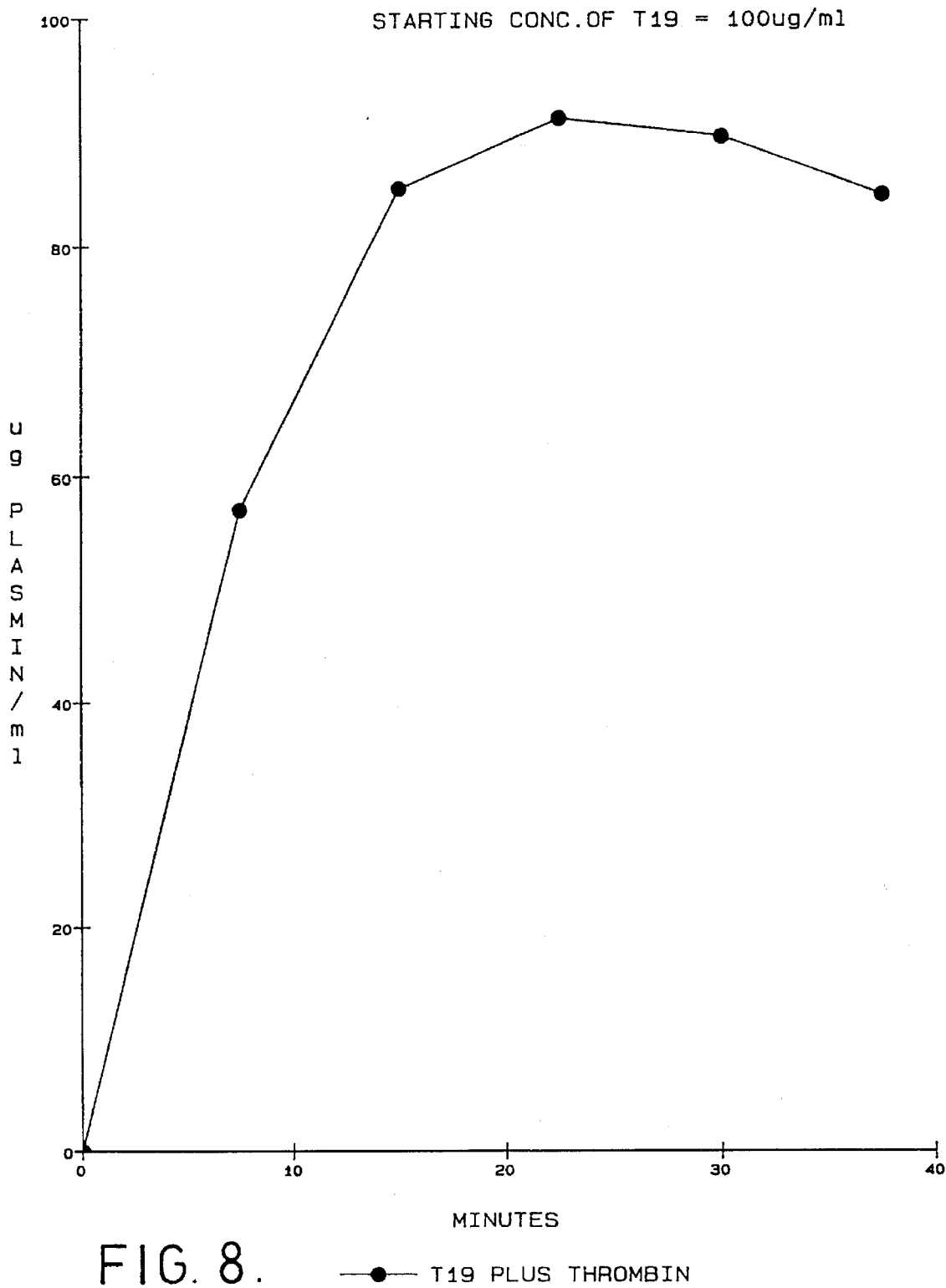
Figure 9:
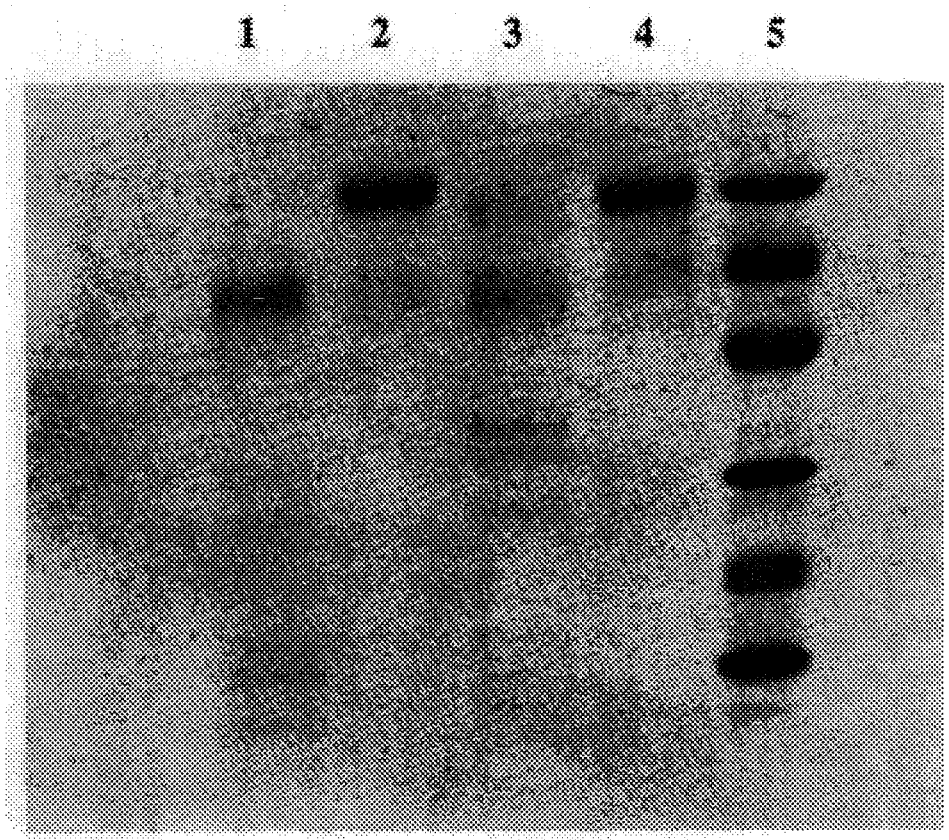
Figure 10:
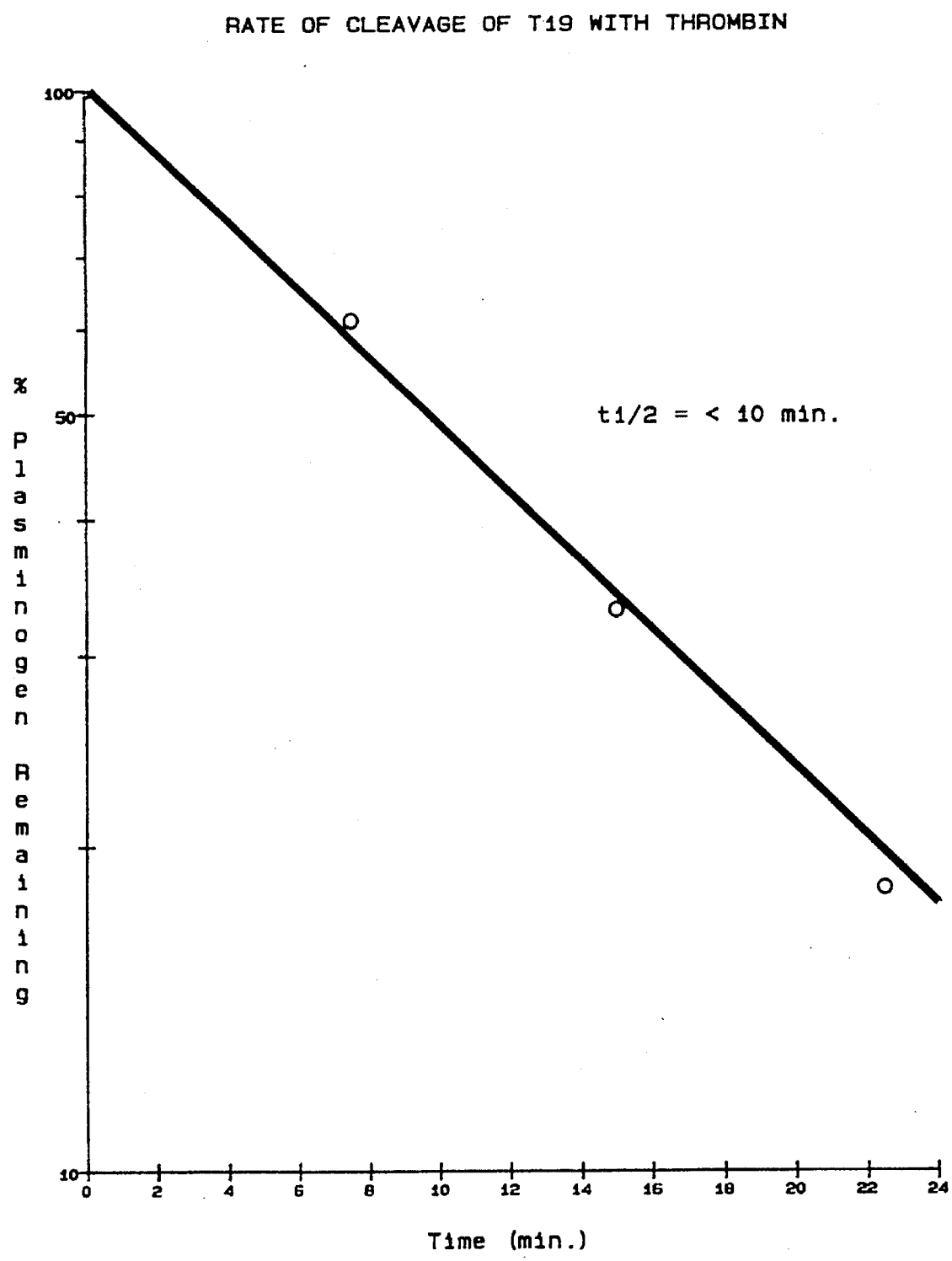

FIG. 7 shows the activation of plasminogen mutants X3, T13 and T19 by factor Xa (for X3) or thrombin (for T13 and T19); X3 is the subject of Examples 5 and 21, T13 is the subject of Examples 13 and 24 and T19 is the subject of Examples 16 and 26;

FIG. 8 shows the activation of plasminogen mutant T19 (Examples 16 and 26) by thrombin, as determined by assay of plasmin;

FIG. 9 shows an SDS-PAGE gel showing cleavage of X2 by Factor Xa and T2 by thrombin; and FIG. 10 shows the rate of cleavage of plasminogen mutant T19 (Examples 16 and 26) with thrombin.

Example 1

The plasmid pSS1 is a signal sequence vector which provides a secretion signal for any gene lacking such a sequence. pGW1 is derived from this vector and pGWH is an expression vector containing a promoter.

Construction of pSS1

1. The plasmid pUC18 (FIG. 1.1) was used as the backbone of the vector as it contains both an *E. coli* origin of replication, which allows production of the plasmid DNA in *E. coli* and an ampicillin resistance gene, allowing selection for the plasmid in *E. coli* (FIG. 1.1). (pUC18 is disclosed in *Gene* 19 259–268 (1982) and *Gene* 26 101–106 (1983) and is deposited at the American Type Culture Collection under deposit no. ATCC 37253.) pUC18 also contains polylinker into which the synthetic DNA was inserted but this polylinker has an EcoRI site which it was necessary to delete before insertion of the synthetic sequence. This was done by cleaving the DNA with EcoRI and treating with mung bean nuclease, a single stranded nuclease, and then religating the plasmid DNA (FIG. 1.2).

2. The modified pUC18 DNA was cleaved with HindIII and BamHI and into these sites a synthetic fragment of DNA: (5'AGCTTCCACCATGAAGTGCTCCTGGGTGAT CTTCTTCCTGATGGCCGTGGT GACCGGCGT-GAACTCGCGAGATCTAGAGTCGACCTG-CAGGATATCGAATTCATT 3' (top strand, SEQ ID NO:41), 5'GATCAATGAATTCGATATCCTGCAGGTC-GACTCTAGATCTCGCGAGTTCACG CCGGTCAC-CACGGCCATCAGGAAGAAGATCACCCAG-GAGCACTTCATGGTGGA 3' (bottom strand, SEQ ID NO:42)) containing an immunoglobulin signal sequence (*Nature*, 331, 173–175 Rogelj et al, 1988) plus a polylinker, which contains a variety of restriction enzyme sites, and also a 237 base pair BclI-BamHI fragment, isolated from SV40 DNA and which contains a polyadenylation signal, were ligated in a three way reaction (FIG. 1.3). Polyadenylation signals from other genes, such as bovine growth hormone, could also be used in the construction of this vector. Remnants of the pUC18 backbone, namely the KpnI and SmaI sites, remained in this construct and so these sites were deleted by digestion of the plasmid DNA with KpnI and BamHI, removal of the fragment and insertion of a bottom strand linker (5'GATCCGTAC 3') which destroys the KpnI and SmaI sites but reforms the BamHI site (FIG. 1.3).

3. In order to make this vector useful for transient expression in COS cells a synthetic 90 base pair SV40 origin of replication (5' TATGAAGACGTCGCCTCCTCAC-
TACTTCTGGAATAGCTCAGAGGCCGAGGC GGC-
CTCGGCCT CTGCATAAATAAAAAAAATT-
AGTCAGGG 3' (top strand, SEQ ID NO:43)),
5'CGCCCTGACTAATTTTTTTATTTATG-
CAGAGGCCGAGGCCGCCTCGGCCTC TGAGCTAT-
TCCAGAAGTAGTGAGGAGGCGACGTCTTCA 3'
(bottom strand, SEQ ID NO:44) was ligated into the NdeI-
NarI sites of pUC18 to replace a 53 base pair fragment (FIG. 1.4).

4. A synthetic DNA sequence (5'AAGCGGCCGCGG
CCATGCCGGCCACTAGTCTCGAGTT 3' (top strand,
SEQ ID NO:45); 5'AACTCGAGACTAGTGGCCG-
GCATGGCCGCGGCCGCTT 3' (bottom strand, SEQ ID
NO:46)), which encodes restriction enzyme sites which cut
infrequently in the mammalian genome and which aids
linearization of the plasmid DNA before transfection, was
ligated into the plasmid at the SspI site to form the promoter-
less vector pSS1 (FIG. 1.5).

5. The nucleotide sequence of the entire plasmid was
confirmed.

Construction of pGW1

Many cDNAs or genes to be expressed already have a
signal sequence and so pSS1 was modified to remove the
secretion signal.

6. The DNA was cleaved with HindIII and NruI, the
fragment removed, and a linker
(5'AGCTTCCCGGGATAGGTACCTCG 3' (top strand,
SEQ ID NO:66), 5'CGAGGTACCTATCCCGGGA 3'
(bottom strand, SEQ ID NO:67)) containing the HindIII,
SmaI, KpnI and NruI sites was inserted (FIG. 1.6). In
addition to removing the signal sequence this also adds two
restriction enzyme sites to the polylinker thus making it
more versatile. This promoterless vector is called pGWI and
its correct assembly was confirmed by nucleotide sequence
analysis of the entire plasmid.

Construction of pGWH

7. The plasmid pSS1 has no promotor or enhancer
sequence. This can be conveniently added by ligating appro-
priate fragments of DNA into the polylinker, for example at
the HindIII site. One promotor/enhancer sequence suitable
for use is the immediate early transcriptional regulatory
region of human cytomegalovirus (HCMV) (*Proc. Natl.
Acad. Sci. USA*, 81, 659–663, Thomsen et al, 1984),
although other regulatory regions could be used e.g. Rous
Sarcoma Virus long terminal repeat (RSV LTR), SV40 early
or late promoter/enhancer region, Mouse mammary tumour
virus (MMTV) LTR, mouse metallothionein promoter. This
was inserted into pGW1 at the HindIII site and then the
orientation was checked by restriction endonuclease diges-
tion. The 5' Hind III site was then deleted by performing a
partial digestion with Hind III, such that only the 5' site was
cleaved. This site was then removed by treatment with mung
bean nuclease and subsequent religation to form pGWH
(FIG. 1.7). The correct assembly of the vector was con-
firmed by nucleotide sequence analysis of the entire plas-
mid.

8. A DNA fragment including the selectable marker gene
gpt and the SV40 early promoter/enhancer sequence and
polyadenylation sequence was cloned into the BamHI site of
the vector to form pGWHg, and allows selection of cells
which have stably integrated the plasmid DNA. Genes
encoding proteins conferring resistance to G418 or
hygromycin, or a variety of metabolic selections, could also
be used.

This particular expression system is preferred because of
its efficiency but its use is not intended to limit the scope of
the present invention. In the literature there are described
many alternative methods of expressing genes in mamma-
lian cells and such expression systems are well known to
those skilled in the art of genetic engineering and have been
at least partially documented by Gorman in "DNA Cloning
Vol. II: A Practical Approach" (D. M. Glover, ed. IRL Press,
Oxford (1985) pp 143–190).

Example 2—Expression of Glu-Plasminogen

Methods that can be used for the isolation of cDNA are
well documented and a procedure that has been used for the
isolation of plasminogen cDNA is summarised in the fol-
lowing protocol. The human plasminogen cDNA has been
cloned and sequenced (Forsgren et al, *FEBS Letters*, 213,
254–260 (1987))

1. The RNA was prepared from fresh human liver using
the guanidine thiocyanate method (Chirgwin et al *Biochem-
istry* 10:5294 (1979)) and purified using an oligo-dT column
(Aviv and Leder *PNAS* 69:1408 (1972))

2. The cDNA library was prepared as described in the
Amersham Protocol ("cDNA Synthesis and Cloning
System", Amersham International plc, 1985). The double
stranded cDNA was ligated into a lambda vector.

3. Plaques were screened for plasminogen cDNA by
hybridization to nitrocellulose replicates using $^{32}$P-labelled
oligonucleotide probes (17 mers), representing the 3' and 5'
ends of plasminogen, in a buffer containing 6×SSC (SSC is
150 mM NaCl, 15 mM sodium citrate), 5×Denhardt's, 0.2%
SDS and 0.1 mg/ml salmon sperm DNA at room temperature
overnight. Filters were washed using 6×SSC, 0.1% SDS at
47° C. Positive plaques were purified, subjected to plasmid
rescue and the packaged recombinant plasmid clones or their
subclones were sequenced by a modification of the dideoxy
method using dATP-5'-α-[35$_S$] thiophosphate (see Methods
section). This cDNA encodes a glu-plasminogen protein of
791 amino acids which corresponds with the length of
plasminogen reported by Forsgren et al, (ibid) and contains
an extra amino acid (Ile65) when compared to the amino
acid sequence determined by protein sequencing (Sottrup-
Jensen et al, ibid). The nucleotide sequence of the cDNA and
the 791 amino acid sequence of glu-plasminogen is shown
in FIG. 2.

Other methods of isolation can be used, for example
mRNA isolated from cells which produce plasminogen can
be prepared using the guanidine thiocyanate method
(Chirgwin et al *Biochemistry* 10:5294 (1979)) and a comple-
mentary first strand of DNA synthesized using reverse
transcriptase. The Polymerase Chain Reaction (PCR) can
then be used to amplify the plasminogen sequence (Saiki R.
et al, *Science*, 239, 487–491 (1988)). The PCR reaction
could also be used to amplify the sequence from DNA
prepared from a genomic or cDNA library which contains
sequences encoding plasminogen. Alternatively, the gene
could be assembled from chemically synthesised oligo-
nucleotides.

Figure 3:
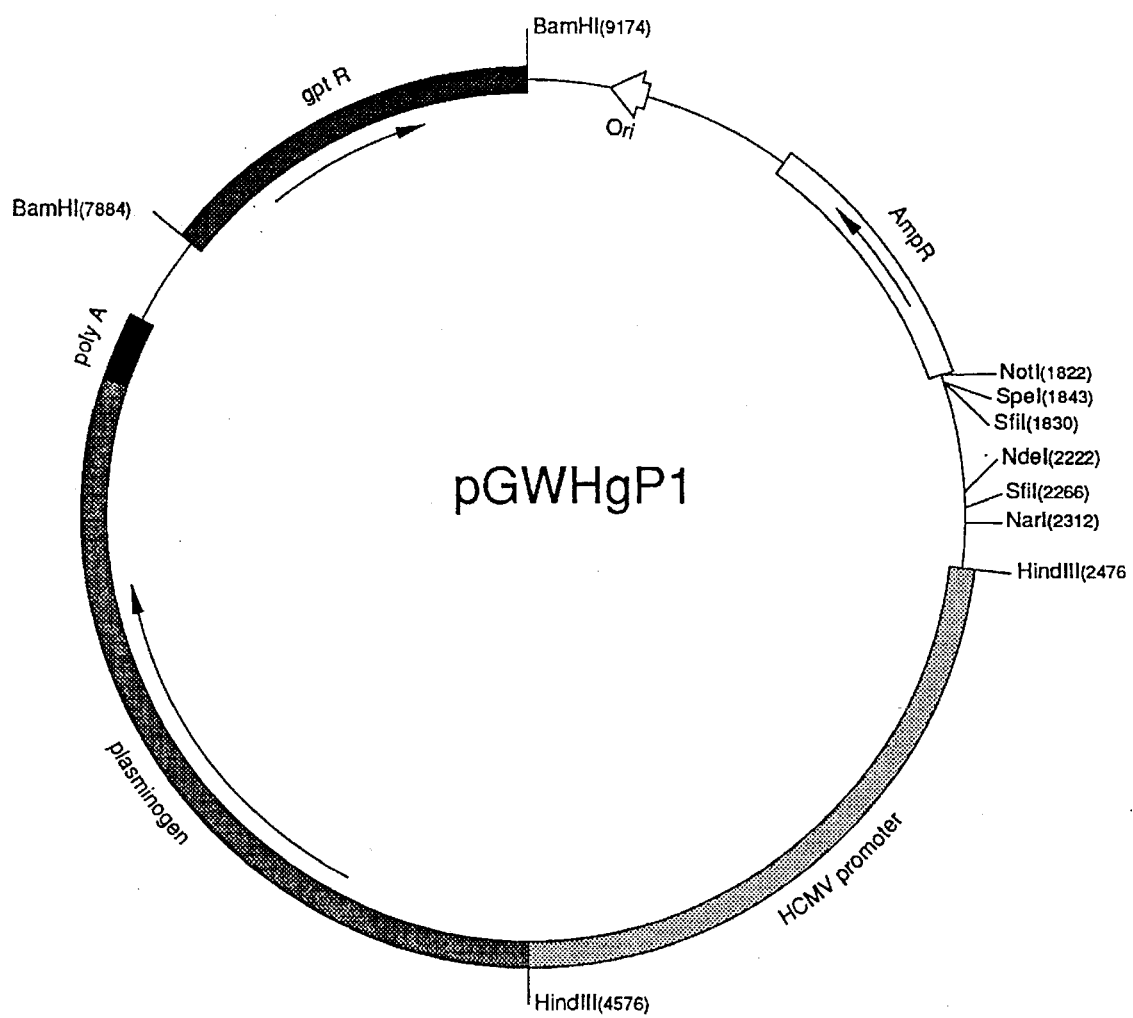
FIG. 3 shows a map of the expression vector pGWHgP1.

The 2.5 kb BalI-SphI glu-plasminogen fragment was
sub-cloned into the polylinker of pUC18 at the SmaI-SphI
sites (FIG. 2). The plasminogen cDNA was then cleaved out
of pUC18 on a KpnI-SphI fragment and ligated into the
vector pGWH to create pGWHP, prepared as described in
Example 1, at the KpnI and EcoRI sites using an EcoRI-SphI
linker (5'AATTCCATG 3'). Thus transcription through the
plasminogen cDNA can initiate at the HCMV promoter/
enhancer (FIG. 3). The selectable marker gpt, expressed
from the SV40 promoter and with a polyadenylation signal
at its 3' end, was cloned into the BamHI site of pGWHP to create pGWHgP1 (FIG. 3) and the orientation checked by restriction enzyme nuclease digestion. Plasmid DNA was introduced into CHO cells by electroporation using 800 V and 25 µF as described in the methods section below. Selective medium (250 µl/ml xanthine, 5 µg/ml mycophenolic acid, 1× hypoxanthine-thymidine (HT)) was added to the cells 24 hours post transfection and the media changed every two to three days. Plates yielding gpt-resistant colonies were screened for plasminogen production using an ELISA assay. Cells producing the highest levels of antigen were re-cloned and the best producers scaled up into flasks with production being carefully monitored. Frozen stocks of all these cell lines were laid down. The cell lines C1.44 and C1.75, which both produce glu-plasminogen at a concentration of >3 mg/liter, were scaled up into roller bottles to provide conditioned medium from which plasminogen protein was purified using lysine SEPHAROSE 4B. (The word SEPHAROSE is a trade mark.) The purified plasminogen was then assayed for its ability to be cleaved to plasmin by tPA or streptokinase using the fibrin agar clot assay. Cleavage of the zymogen was also established using SDS PAGE (*Nature*, 227, 680, Laemmli, 1970).

The techniques of genetic manipulation, expression and protein purification used in the manufacture of this wild type plasminogen, as well as those of the modified plasminogen examples to follow, are well known to those skilled in the art of genetic engineering. A description of most of the techniques can be found in one of the following laboratory manuals: "Molecular Cloning" by T. Maniatis, E. F. Fritsch and J. Sambrook published by Cold Spring Harbor Laboratory, Box 100, New York, or "Basic Methods in Molecular Biology" by L. G. Davis, M. D. Dibner and J. F. Battey published by Elsevier Science publishing Co Inc, New York.

Additional and modified methodologies are detailed in the methods section below.

Example 3—Construction and Expression of X1

Plasminogen analogues which are altered around the Arg(561), Val(562) cleavage sites have been constructed in order to modify the site and allow recognition and cleavage by alternative enzymes. X1 is a plasminogen analogue in which the amino acid residue Pro(559) is replaced by Ile and Glu (FIG. 4). This site was based on a Factor Xa cleavage site in prothrombin. The modification strategy in this example was to sub-clone the 1.87 Kb KpnI-HincII fragment, from the plasminogen cDNA in a pUC18 vector, into the single stranded bacteriophage M13mp18 to facilitate the mutagenesis. Single strand template was prepared and the mutations made by oligonucleotide directed mismatch mutagenesis. In this case a 21 base long oligonucleotide (5'CCCTTCCCTCGATACATTTCT 3', SEQ ID NO:47) was used to direct the mutagenesis. Clones carrying the mutation were identified by sequencing and then fully sequenced to ensure that no other mutation had inadvertently been introduced. Replicative form (RF) DNA was then prepared and the mutation transferred into the expression vector containing the Glu plasminogen (as described in Example 2) by replacing the wild type KpnI-EcoRV fragment with the mutated fragment. The pGWHg plasmid carrying the mutant plasminogen was then linearized with the restriction endonuclease NotI and introduced into CHO cells by electroporation. The expression protocol was then the same as that described in Example 2. The cell line used to produce this mutant protein is C7.9. Activation and cleavage of this mutant with purified Factor Xa was investigated as described for Examples 20 and 29.

Example 4—Construction and Expression of X2

The procedure of Example 3 was generally followed except that the primer used was the 22 mer (5'CCTTCCCTCGATGCCACATTTC 3', SEQ ID NO:48). The resulting mutant derivative of plasminogen has the following amino acid changes: Pro(559) to Gly, Gly(560) to Ile and addition of Glu and Gly before Arg(561) (FIG. 4). This cleavage site is based on a Factor Xa cleavage site in prothrombin. The cell line C8.24 was scaled up to produce this mutant protein. Otherwise, the procedure of Example 3 was generally followed. Activation and cleavage of this mutant was investigated as described in Examples 20 and 27.

Example 5—Construction and Expression of X3

In X3, Pro(559) has been substituted by Gly, Ala, Ile and Glu using the 48 mer (5'CCCCCCCCACAACCCTTCCCTCTATTGCACCACATTTCTTCGGCTCCAC 3', SEQ ID NO:49) (FIG. 4). The cell line C37.4 has been used to produce this protein which has a cleavage site based on a Factor Xa cleavage site in prothrombin. Otherwise, the procedure of Example 3 was generally followed. Activation of this mutant is described in Example 21 below.

Example 6—Construction and Expression of X5

X5 has Pro(559) replaced by Gly, Tyr, Ile and Asp using a 48 mer (5'CCCCCCCACAACCCTTCCGTCTATGTAACCACATTTCTTCGGCTCCAC 3', SEQ ID NO:50) (FIG. 4). The cell line C39.7 has been used to produce this protein which has a cleavage site based on a Factor Xa cleavage site in prothrombin. Otherwise, the procedure of Example 3 was generally followed. Activation of this mutant is described in Example 21 below.

Example 7—Construction and Expression of X6

In addition to the mutation in X5, X6 has Val(561) replaced by Ile (FIG. 4). This was made using the 52 mer (5'CACACCCCCCCACAATCCTTCCGTCTATGTAACCACATTTCTTCGGCTCCAC 3', SEQ ID NO:51). The cell line C36.1 has been used to produce this protein. Otherwise, the procedure of Example 3 was generally followed. Activation of this mutant is described in Example 21 below.

Example 8—Construction and Expression of T1

T1 is a plasminogen derivative in which Pro(559) and Gly(560) have been interchanged to give Gly at position 559 and Pro at 560 (FIG. 5). This cleavage site mimics the thrombin cleavage site at Arg(19)-Val(20) in the fibrinogen A alpha chain. The procedure of Example 3 was generally followed except that the primer used was the 21 mer (5'CAACCCTTGGACCACATTTCT 3', SEQ ID NO:52). The cell line producing the T1 mutant is C6.23. Activation and cleavage of this protein are described in Examples 22 and 28 below.

Example 9—Construction and Expression of T2

T2 is a plasminogen derivative which has been modified from wild type plasminogen in the same way as T1 but an extra Gly amino acid has been added between Gly(559) and Pro(560) (FIG. 5). The procedure of Example 3 was generally followed except that the primer used to make this mutant is a 22 mer (5'ACCCTTGGACCACCACATTTCT 3', SEQ ID NO:53). The cell line C5.16 was used to produce this mutant protein. Activation and cleavage of this mutant are shown in Examples 22 and 28 below.

Example 10—Construction of T6

In the T6 protein there are two sites of amino acid change. The amino acids Pro(559), Gly(560), Arg(561), Val (562) have been replaced by six amino acids to become Gly(559), Val(560), Val(561), Pro(562), Arg(563), Gly(564). In addition to these changes, Val(553), Lys(556), Lys(567) have been replaced by Leu, Glu and Leu respectively using a 61 mer (5'GGGCCACACACCCCCCCACTCCCCTAGGCACAACTCCACATAGCTCCGGCTCCAGTTGAGG 3', SEQ ID NO:54) (FIG. 5). This modification is based on a thrombin cleavage site in Factor XIII. The cell line C45.1 was used to produce this protein. Otherwise, the procedure of Example 3 was generally followed. Activation and cleavage of this protein is described in Examples 23 and 29 below.

Example 11—Construction and Expression of T7

In another modification based on a thrombin cleavage site in Factor XIII, T7 incorporates the first set of changes described for T6 namely the replacement of Pro(559), Gly (560), Arg(561), Val(562) by six amino acids to become Gly(559), Val(560), Val(561), Pro(562), Arg(563), Gly(564). In addition Val(553), Lys(556) and Lys(557) have been replaced by Leu, Gln and Leu respectively using the 60 mer (5'GGCCACACACCCCCCCACTCCCCTAGGCACAAC TCCACATAGTTGCGGCTCCAGTTGAGG 3', SEQ ID NO:55) (FIG. 5). The cell line C26.5 was used to produce this protein. Otherwise, the procedure of Example 3 was generally followed. Activation and cleavage of this protein is described in Examples 23 and 29 below.

Example 12—Construction and Expression of T8

T8 is based on the thrombin cleavage site in Factor XIII and in this protein Pro(559), Gly(560), Arg(561), Val(562) have been replaced by Val, Glu, Leu, Gln, Gly, Val, Val, Pro, Arg, Gly using a 61 mer (5'CACACACCCCCCCACTCCCCTAGGCACTACTC CTTGTAGTTCTACACATTTCTTCGGCTCC 3', SEQ ID NO:56) (FIG. 5). The cell line C34.5 has been used to produce this protein. Otherwise, the procedure of Example 3 was generally followed. Activation and cleavage of this protein is described in Examples 23 and 29 below.

Example 13—Construction and Expression of T13

In the plasminogen derivative T13 the two amino acids Pro(559), Gly(560), have been replaced by three amino acids Val, Val and Pro using a 41 mer (5'CACCCCCCCA CAACCCTAGGTACAACACATTTCTTCGGCTC 3', SEQ ID NO:57) (FIG. 5). The cell line C51.1 was used to produce this protein. Otherwise, the procedure of Example 3 was generally followed. Activation and cleavage of this protein is described in Examples 24 and 29 below.

Example 14—Construction and Expression of T14

The plasminogen analogue T14 has a thrombin cleavage site based on a site cleaved by thrombin in calcitonin. In this mutant the amino acids Gly and Tyr are inserted between Cys(558) and Pro(559) and in addition Gly(560) is deleted (FIG. 5). These mutations were made using a 41 mer (5'CACCCCCCCACAACCCTAGGGTATCCACATTTCT TCGGCT 3', SEQ ID NO:58). The cell line used to produce this protein was C61.1. Otherwise, the procedure of Example 3 was generally followed.

Example 15—Construction and Expression of T17

The protein T17 has a cleavage site based on a site cleaved by thrombin in cholecystokinin. This protein has Ser inserted between Pro559 and Gly 560 and was made using a 38 mer (5'CACCCCCCCACAACCCTTCCACTAGGAC ATTTCTTCGG 3', SEQ ID NO:59) (FIG. 5). The cell line C49.7 was used to produce this protein. Otherwise, the procedure of Example 3 was generally followed. Activation and cleavage of this protein is described in Examples 25 and 29 below.

Example 16—Construction and Expression of T19

The cleavage site of this protein is based on a thrombin cleavage site in factor XIII. This mutant differs from T8 in that the P1' amino acid is Val rather than Gly. Cleavage produces two chain T19 plasmin with a native light chain sequence. In this protein Pro(559), Gly(560), Arg(561) have been replaced by Val, Glu, Leu, Gln, Gly, Val, Val, Pro, Arg using a 61 mer (5'CACACCCCCCCACAACCCTTGGG ACTACTCCCTGCAATTCTACACATTTCT TCGGCTCCAC 3', SEQ ID NO:60) (FIG. 5). The cell line, C53.5, was used to produce the protein. Otherwise, the procedure of Example 3 was generally followed. The activation and cleavage analysis of this protein is presented in Examples 26 and 29 below.

Example 17—Construction and Expression of T20

The cleavage site of this protein is similar to T19 but the amino terminal sequence of the plasmin light chain generated by cleavage has Val(562), Val(563) deleted. In this protein Pro(559), Gly(560), Arg(561), Val(562) and Val (563) have been replaced by Val, Glu, Leu, Gln, Gly, Val, Val, Pro, Arg using a 58 mer (5'GGCCACACACCCCC CCCTTGGGACTACTCCCTGCAATTCTA- CACATTTCTTCGGCTCC 3', SEQ ID NO:61) (FIG. 5). The cell line C54.2 was used to produce protein. Otherwise, the procedure of Example 3 was generally followed.

Example 18—Construction and Expression of T21

This mutant differs from T6 in that the P1' amino acid is Val rather than Gly. Cleavage produces two chain T21 plasmin with a native light chain sequence. The cDNA encoding this protein was made using the T6 cDNA template, described in Example 10, and the 23 mer (5'CACCCCCCCACTACCCTAGGCAC 3', SEQ ID NO:62) (FIG. 5). The cell line C55.9 has been used to produce this protein. Otherwise, the procedure of Example 3 was generally followed.

Example 19—Construction and Expression of T22

This mutant differs from T7 in that the P1' amino acid is Val rather than Gly. Cleavage produces two chain T22 plasmin with a native light chain sequence (FIG. 5). The cDNA encoding this protein was made in a T7 cDNA background, as described in Example 11, using the 23 mer described for T21. The cell line C56.11 has been used to produce this protein. Otherwise, the procedure of Example 3 was generally followed.

Example 20—Activation of X1 and X2

Figure 6:
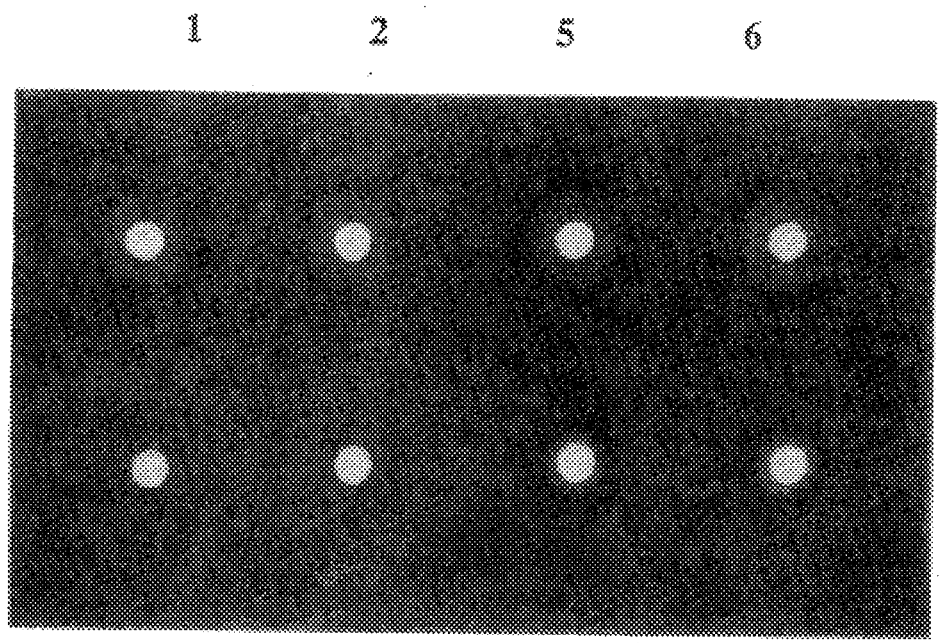
FIG. 6 shows activation of X2 by Factor Xa and T2 by thrombin on a fibrin agar gel.

Activation of the X1 and X2 proteins to plasmin by Factor Xa was tested using a fibrin lysis assay. Generation of plasmin is detected by the appearance of a zone of clearance developing in a fibrin-agarose gel as described in Method 12.1 (see Methods section below). 25 µl lots of purified plasminogen mutant (635 µg/ml) were incubated with 2.5 µl purified Factor Xa (0.35 µg) at 37° C. Generation of plasmin was assayed by adding 10 µl samples from the incubation to wells in a fibrin agar gel. Samples of plasminogen mutant incubated with Factor Xa gave a zone of clearance on the gel which was not present in control samples which had not been incubated with Factor Xa. Activation of X2 to plasmin by Factor Xa is shown in FIG. 6.

Example 21—Activation of X3, X5 and X6

Purified X3 protein was assayed for activation using the linked chromogenic assay (see Method 12.3). Results of this assay are shown in FIG. 7 in which the increase in absorbance at 405 nm with time demonstrates that plasmin activity is generated upon incubation of X3 with Factor Xa. Similarly, X5 and X6 were shown to be activated upon incubation with Factor Xa.

Example 22—Activation of T1 and T2

The purified mutant proteins T1 and T2 were assayed for activation as described in Example 20 except that the mutant proteins were preincubated with thrombin (2551 plasminogen mutant (120 µg/ml) was incubated with 2.5 µl thrombin (0.69 units)) and the wells in the fibrin gel were pretreated with hirudin to inhibit any activating effect of the thrombin which was used to make the gel. Both mutants were activated by thrombin as samples incubated with thrombin produced a zone of clearance on the gel. Zones of clearance were not produced by control samples which had not been incubated with thrombin. The results for T2 are shown in FIG. 6.

Example 23—Activation of T6, T7 and T8

The mutant proteins were assayed for activation using the linked chromogenic assay (see Method 12.3). This assay demonstrated that T6, T7 and T8 are not activated by thrombin (although they are cleaved—see Example 29).

Example 24—Activation of T13

Purified T13 protein was assayed using the linked chromogenic assay as described in Example 23. Results of this assay are shown in FIG. 7 in which the increase in absorbance at 405 nm with time demonstrates that T13 is activated by thrombin. Activation was also detected using the direct chromogenic assay as described in Example 26.

Example 25—Activation of T17

Purified T17 protein was assayed using the linked chromogenic assay as described in Example 23. This assay demonstrated that thrombin activates T17.

Example 26—Activation of T19

Purified T19 protein was assayed using the linked chromogenic assay as described in Example 23. Results of this assay are shown in FIG. 7 in which the increase in absorbance at 405 nm with time demonstrates that T19 is activated by thrombin.

The mutant protein T19 was also analysed using a direct chromogenic assay which allows quantitation of plasmin generated by activation (see Method 12.2). Results of this assay are shown in FIG. 8 in which the generation of plasmin with time demonstrates that T19 is activated by thrombin.

Example 27—Cleavage of X Mutants

Samples of 25 µg of X plasminogen mutants were incubated with 1.5 µg Factor Xa in 0.25 ml buffer and cleavage analysis was performed as described in Method 11. FIG. 9 shows that the X2 plasminogen band at approximately 92 kDa was cleaved to form a heavy chain plasmin band at approximately 66 kDa. This indicates that the mutant amino acid sequence that we have introduced is cleaved by Factor Xa and that the activation demonstrated for X2 in Example 20 is a result of cleavage of the plasminogen analogue to produce plasmin.

Example 28—Cleavage of T1 and T2

Cleavage analyses of the purified proteins T1 and T2 were performed as described in Example 27 except that thrombin (1.5 µg) was used instead of Factor Xa. Cleavage of T2 to plasmin by thrombin is shown in FIG. 9 thus confirming that the activation demonstrated in Example 24 is a result of thrombin cleavage.

Example 29—Cleavage of T6, T7, T8, T13, T17 and T19

Samples of 12.5 µg plasminogen mutant were incubated with 2.8 µg thrombin as described in Method 11. The time course of cleavage of the plasminogen mutants was determined by quantitative gel scanning and the times for 50% cleavage of T6, T7, T8, T13, and T19 were 13, 40, 15, 70 and less than 10 minutes respectively while the cleavage time for T17 was approximately 30 hours. Gel scan data for cleavage of T19 (disappearance of the plasminogen band) are shown in FIG. 10.

Example 30—Construction of Lys-3

A cDNA encoding a lys-plasminogen in which the native plasminogen signal sequence lies adjacent to the Glu(76) residue has been made by deleting the 75 amino terminal amino acids of glu-plasminogen by loop out mutagenesis using a 35 mer (5'CTGAGAGATACACTTTCTTTTCTCCTTGACCTGAT 3', SEQ ID NO:63). Otherwise, the procedure of Example 3 was generally followed.

Example 31—Construction of Lys-4

In this lys-plasminogen, 77 amino acids between Gly(19) of the signal sequence and Lys(78) of glu-plasminogen were deleted by loop out mutagenesis using a 29 mer (5'CTGAGAGATACACTTTTCCTTGACCTGAT 3', SEQ ID NO:64). Otherwise, the procedure of Example 3 was generally followed.

Example 32—Construction of Lys-5

In this lys-plasminogen, 76 amino acids between Gly(19) of the signal sequence and Lys(77) of glu-plasminogen were deleted by loop out mutagenesis using a 32 mer (5'CTGAGAGATACACTTTCTTTCCTTGACCTGAT 3', SEQ ID NO:65). Otherwise, the procedure of Example 3 was generally followed.

METHODS

1) Mung Bean Nuclease Digestion 10 units of mung bean nuclease was added to approximately 1 µg DNA which had been digested with a restriction enzyme in a buffer containing 30 mM NaOAc pH5.0, 100 mM NaCl, 2 mM ZnCl, 10% glycerol. The mung bean nuclease was incubated at 37° for 30 minutes, inactivated for 15 minutes at 67° before being phenol extracted and ethanol precipitated.

2) Oligonucleotide Synthesis

The oligonucleotides were synthesised by automated phosphoramidite chemistry using cyanoethyl phosphoramidites. The methodology is now widely used and has been described (Beaucage, S. L. and Caruthers, M. H. *Tetrahedron Letters* 24, 245 (1981) and Caruthers, M. H. *Science* 230, 281–285 (1985)).

3) Purification of Oligonucleotides

The oligonucleotides were de-protected and removed from the CPG support by incubation in concentrated $NH_3$. Typically, 50 mg of CPG carrying 1 micromole of oligonucleotide was de-protected by incubation for 5 hours at 70° in 600 µl of concentrated $NH_3$. The supernatant was transferred to a fresh tube and the oligomer precipitated with 3 volumes of ethanol. Following centrifugation the pellet was dried and resuspended in 1 ml of water. The concentration of crude oligomer was then determined by measuring the absorbance at 260 nm.

For gel purification 10 absorbance units of the crude oligonucleotide was dried down and resuspended in 15 µl of marker dye (90% de-ionised formamide, 10 mM tris, 10 mM borate, 1 mM EDTA, 0.1% bromophenol blue). The samples were heated at 90° for 1 minute and then loaded onto a 1.2 mm thick denaturing polyacrylamide gel with 1.6 mm wide slots. The gel was prepared from a stock of 15% acrylamide, 0.6% bisacrylamide and 7M urea in 1×TBE and was polymerised with 0.1% ammonium persulphate and 0.025% TEMED. The gel was pre-run for 1 hr. The samples were run at 1500 V for 4–5 hours. The bands were visualised by UV shadowing and those corresponding to the full length product cut out and transferred to micro-testubes. The oligomers were eluted from the gel slice by soaking in AGEB (0.5M ammonium acetate, 0.01M magnesium acetate and 0.1% SDS) overnight. The AGEB buffer was then transferred to fresh tubes and the oligomer precipitated with three volumes of ethanol at 70° for 15 mins. The precipitate was collected by centrifugion in an Eppendorf microfuge for 10 mins, the pellet washed in 80% ethanol, the purified oligomer dried, redissolved in 1 ml of water and finally filtered through a 0.45 micron micro-filter. (The word EPPENDORF is a trade mark.) The concentration of purified product was measured by determining its absorbance at 260 nm.

4) Kinasing of Oligomers 100 pmole of oligomer was dried down and resuspended in 20 µl kinase buffer (70 mM Tris pH 7.6, 10 mM $MgCl_2$, 1 mM ATP, 0.2 mM spermidine, 0.5 mM dithiothreitol). 10 u of T4 polynucleotide kinase was added and the mixture incubated at 37° for 30 mins. The kinase was then inactivated by heating at 70° for 10 mins.

5) Dideoxy Sequencing

The protocol used was essentially as has been described (Biggin, M. D., Gibson, T. J., Hong, G. F. *P.N.A.S.* 80 3963–3965 (1983). Where appropriate the method was modified to allow sequencing on plasmid DNA as has been described (Guo, L-H., Wu R *Nucleic Acids Research* 11 5521–5540 (1983).

6) Transformation

Transformation was accomplished using standard procedures. The strain used as a recipient in the cloning using plasmid vectors was HW87 which has the following genotype:

araD139(ara-leu)de17697 (lacIPOZY)de174 galU galK hsdR rpsL srl recA56

RZ1032 is a derivative of *E. coli* that lacks two enzymes of DNA metabolism: (a) dUTPase (dut) which results in a high concentration of intracellular dUTP, and (b) uracil N-glycosylase (ung) which is responsible for removing mis incorporated uracils from DNA (Kunkel et al, *Methods in Enzymol.*, 154, 367–382 (1987)). Its principal benefit is that these mutations lead to a higher frequency of mutants in site directed mutagenesis. RZ1032 has the following genotype:

HfrKL16PO/45[lysA961–62), dutl, ungl, thil, re[A], Zbd-279::Tn10, supE44

JM103 is a standard recipient strain for manipulations involving M13 based vectors.

7) Site Directed Mutagenesis

Kinased mutagenesis primer (2.5 pmole) was annealed to the single stranded template DNA, which was prepared using RZ1032 as host, (1 µg) in a final reaction mix of 10 µl containing 70 mM Tris, 10 mM $MgCl_2$. The reaction mixture in a polypropylene micro-testube (EPPENDORF) was placed in a beaker containing 250 ml of water at 70° C. for 3 minutes followed by 37° C. for 30 minutes. The annealed mixture was then placed on ice and the following reagents added: 1 µl of 10×TM (700 mM Tris, 100 mM $MgCl_2$ pH7.6), 1 µl of a mixture of all 4 deoxyribonucleotide triphosphates each at 5 mM, 2 µl of T4 DNA ligase (100 u), 0.5 µl Klenow fragment of DNA polymerase and 4.5 µl of water. The polymerase reaction mixture was then incubated at 15° for 4–16 hrs. After the reaction was complete, 180 µl of TE (10 mM Tris, 1 mM EDTA pH8.0) was added and the mutagenesis mixture stored at −20° C.

For the isolation of mutant clones the mixture was then transformed into the recipient JM103 as follows. A 5 ml overnight culture of JM103 in 2×YT (1.6% Bactotryptone, 1% Yeast Extract, 1% NaCl) was diluted 1 in a 100 into 50 ml of pre-warmed 2×YT. The culture was grown at 37° with aeration until the $A_{600}$ reached 0.4. The cells were pelleted and resuspended in 0.5 vol of 50 mM $CaCl_2$ and kept on ice for 15 mins. The cells were then re-pelleted at 4° and resuspended in 2.5 ml cold 50 mM $CaCl_2$. For the transfection, 0.25, 1, 2, 5, 20 and 50 µl aliquots of the mutagenesis mixture were added to 200 µl of competent cells which were kept on ice for 30 mins. The cells were then heated shocked at 42° for 2 mins. To each tube was then added 3.5 ml of YT soft agar containing 0.2 ml of a late exponential culture of JM103, the contents were mixed briefly and then poured onto the surface of a pre-warmed plate containing 2×YT solidified with 1.5% agar. The soft agar layer was allowed to set and the plates then incubated at 37° overnight.

Single stranded DNA was then prepared from isolated clone as follows: Single plaques were picked into 4 ml of 2×YT that had been seeded with 10 µl of a fresh overnight culture of JM103 in 2×YT. The culture was shaken vigorously for 6 hrs. 0.5 ml of the culture was then removed and added to 0.5 ml of 50% glycerol to give a reference stock that was stored at −20°. The remaining culture was centrifuged to remove the cells and 1 ml of supernatant carrying the phage particles was transferred to a fresh EPPENDORF tube. 250 µl of 20% PEG6000, 250 mM NaCl was then added, mixed and the tubes incubated on ice for 15 mins. The phage were then pelleted at 10,000 rpm for 10 mins, the supernatant discarded and the tubes re-centrifuged to collect the final traces of PEG solution which could then be removed and discarded. The phage pellet was thoroughly resuspended in 200 µl of TEN (10 mM Tris, 1 mM EDTA, 0.3M NaOAc). The DNA was isolated by extraction with an equal volume of Tris saturated phenol. The phases were separated by a brief centrifugation and the aqueous phase transferred to a clean tube. The DNA was re-extracted with a mixture of 100 µl of phenol, 100 µl chloroform and the phases again separated by centrifugation. Traces of phenol were removed by three subsequent extractions with chloroform and the DNA finally isolated by precipitation with 2.5 volumes of ethanol at −20° overnight. The DNA was pelleted at 10,000 rpm for 10 min, washed in 70% ethanol, dried and finally resuspended in 50 µl of TE.

8) Electroporation

Chinese hamster ovary cells (CHO) or the mouse myeloma cell line p3×63-Ag8.653 were grown and harvested in mid log growth phase. The cells were washed and resuspended in PBS and a viable cell count was made. The cells were then pelleted and resuspended at $1\times10^7$ cells/ml. 40 µg of linearised DNA was added to 1 ml of cells and allowed to stand on ice for 15 mins. One pulse of 800 V/25 µF was administered to the cells using a commercially available electroporation apparatus (BIORAD GENE PULSER—trade mark). The cells were incubated on ice for a further 15 mins and then plated into either 10×96 well plates with 200 µl of conditioned medium per well (DMEM, 5% FCS, Pen/Strep, glutamine) or 10×15 cm dishes with 15 mls medium in each dish and incubated overnight. After 24 hrs the medium was removed and replaced with selective media containing xanthine (250 µg/ml), mycophenolic acid (5 µg/ml) and 1×hypoxanthine-thymidine (HT). The cells were fed every third day.

After about 14 days gpt resistant colonies are evident in some of the wells and on the plates. The plates were screened for plasminogen by removing an aliquot of medium from each well or plate and assayed using an ELISA assay. Clones producing plasminogen were scaled up and the expression level monitored to allow the selection of the best producer.

9) ELISA for Human Plasminogen

ELISA plates (Pro-Bind, Falcon) are coated with 50 µl/well of goat anti-human plasminogen serum (Sigma) diluted 1:1000 in coating buffer (4.0 g $Na_2CO_3(10.H_2O)$, 2.93 g $NaHCO_3$ per liter $H_2O$, pH 9.6) and incubated overnight at 4° C. Coating solution is then removed and plates are blocked by incubating with 50 µl/well of PBS/ 0.1% casein at room temperature for 15 minutes. Plates are then washed 3 times with PBS/0.05% Tween 20. Samples of plasminogen or standards diluted in PBS/Tween are added to the plate and incubated at room temperature for 2 hours. The plates are then washed 3 times with PBS/Tween and then 50 µl/well of a 1:1000 dilution in PBS/Tween of a monoclonal antihuman plasminogen antibody (American Diagnostica, New York, USA) is added and incubated at room temperature for 1 hour. The plates are again washed 3 times with PBS/Tween and then 50 µl/well of horse radish peroxidase conjugated goat anti-mouse IgG (Sigma) is added and incubated at room temperature for 1 hour. The plates are washed 5 times with PBS/Tween and then incubated with 100 µl/well of peroxidase substrate (0.1M sodium acetate/ citric acid buffer pH 6.0 containing 100 mg/liter 3,3',5,5'-tetramethyl benzidine and 13 mM $H_2O_2$. The reaction is stopped after approximately 5 minutes by the addition of 25 µl/well of 2.5M sulphuric acid and the absorbance at 450 nm read on a platereader.

10) Purification of Plasminogen Variants

Plasminogen variants are purified in a single step by chromatography on lysine SEPHAROSE 4B (Pharmacia). A column is equilibrated with at least 10 column volumes of 0.05M sodium phosphate buffer pH 7.5. The column is loaded with conditioned medium at a ratio of 1 ml resin per 0.6 mg of plasminogen variant as determined by ELISA using human glu-plasminogen as standard. Typically 400 ml of conditioned medium containing plasminogen are applied to a 10 ml column (H:D=4) at a linear flow rate of 56 ml/cm/h at 4° C. After loading is complete, the column is washed with a minimum of 5 column volumes of 0.05M phosphate buffer pH 7.5 containing 0.5M NaCl until non-specifically bound protein ceases to be eluted. Desorption of bound plasminogen is achieved by the application of 0.2M epsilon-amino-caproic acid in de-ionised water pH 7.0. Elution requires 2 column volumes and is carried out at a linear flow rate of 17 ml/cm/h. Following analysis by SDS PAGE to check purity, epsilon-amino-caproic acid is subsequently removed and replaced with a suitable buffer, eg Tris, PBS, HEPES or acetate, by chromatography on pre-packed, disposable, PD10 columns containing SEPHADEX G-25M (Pharmacia). (The word SEPHADEX is a trade mark.) Typically, 2.5 ml of each plasminogen mutant at a concentration of 0.3 mg/ml are processed in accordance with the manufacturers' instructions. Fractions containing plasminogen, as determined by $A_{280}$ are then pooled.

11) Cleavage

Plasminogen analogues are assessed for susceptibility to cleavage by proteolytic activators using SDS PAGE under reducing conditions. Typical incubation volumes of 0.125 ml in 100 mM Tris HCl pH 7.4 and 1 mM $Ca^{2+}$ consist of plasminogen analogue, at concentrations shown in the examples, and the activators Factor Xa or thrombin, at concentrations shown in the examples. Incubations are performed at 37° C. Control incubations are performed under the same conditions in the absence of activators. The activation reactions were stopped by precipitating the protein by the addition of trichloroacetic acid to a final concentration of 20% and standing at 4° C. for >4 hours. The precipitates were then pelleted, washed with acetone and resuspended in SDS PAGE sample buffer (0.1 m Tris pH6.8, 10% glycerol, 1% SDS, 0.5% mercaptoethanol and 0.05% bromophenol blue). The samples were analysed either on 8–25% gradient gels or 12% gels. The resulting gels were analysed using a SHIMADZU Gel Scanner which scans the gel and calculates the concentration of protein in bands by determining the area under the peaks. (The word SHIMADZU is a trade mark.) The rate of cleavage of plasminogen was thus determined by measuring the disappearance of the plasminogen band at approximately 92 kDa and the appearance of the plasmin heavy chain band at approximately 66 kDa.

12) Activation 12.1 Fibrin Clot Lysis Assay

In the fibrin lysis assay, plasmin activity is detected by the appearance of a zone of clearance developing (due to fibrin dissolution) in a fibrin-agarose gel. The gel is made in a 1% low gelling temperature agarose gel, buffered in 0.1M Tris HCl pH7.4, 0.15M NaCl, 2 mM $CaCl_2$ by adding plasminogen-free fibrinogen dissolved in 0.9%(w/v) NaCl, to a final concentration of 1 mg/ml. 6 units of thrombin are added to convert the fibrinogen to fibrin and the solution is then poured onto a sheet of GEL-BOND and left to set. (The expression GEL-BOND is a trade mark.) Before use, wells are punched in the gel and the agarose plugs are removed. Samples of 5–10 µl are loaded into the wells and the gel is incubated in a humidity chamber at 37° C. overnight (17–20 hours), or for an appropriate time for a zone of lysis to appear. The gel is then soaked in 7.5% acetic acid for 1 hour, stained in fast green (2% solution) for 1–10 minutes and then destained with 40% methanol, 10% acetic acid for at least 2 hours. The gel is then drained and placed at 37° C. overnight to dry. The diameter of the zones of lysis can be measured and compared to those made by the standards e.g. wild type plasminogen activated with tPA or u-PA.

12.2 Direct Chromogenic Assay and Time Course of Activation

Plasminogen analogue (12.5 μg) was incubated with thrombin (2.8 μg) at 37° C. in 125 μl of a buffer containing 100 mM Tris HCl pH 7.4 and 1 mM CaCl$_2$. Aliquots were removed at intervals and assayed for plasmin content in a chromogenic assay as described below. When thrombin was used as activator the thrombin inhibitor hirudin was added in slight molar excess to stop the activation reaction and the samples were stored at −70° C. When Factor Xa was used as activator samples were immediately snap frozen to stop the activation reaction. Plasmin was measured using cleavage of the tripeptide chromogenic substrate, S2251 (Kabi). Aliquots of the sample (25 μl) were mixed with 75 μl buffer (50 mM Tris HCl, 0.1M EDTA, 0.0005% Triton X100, pH 8.0) containing 0.6 mM S2251, in 96 well plates (Costar). The plates were incubated at 37° C. for 2 hours. The reaction was terminated by adding 25 μl 0.5M acetic acid and the absorbance read at 405 nm using an automatic plate reader (Dynatech). Quantitation was performed by comparison with a standard plasmin preparation.

12.3 Linked Chromogenic Assay

A modification of the chromogenic assay was developed to measure the time course of activation of mutant plasminogens more directly. In this assay, mutant plasminogen and activator are incubated together in the presence of S2251 and plasmin produced by activation directly cleaves the chromogenic substrate leading to an increase in absorbance at 405 nm. The assay was performed in a total volume of 880 μl in a buffer containing 50 mM Tris HCl, 0.1 mM EDTA, 0.005% Triton X100 and 0.1% HSA. The chromogenic substrate S2251 was added to a final concentration of 0.35 mg/ml and the mutant protein concentration used was 3 μg/ml. In the case of thrombin activation, thrombin was added to a final concentration of 1 or 0.2 μg/ml. Factor Xa was added to a final concentration of 1.5 or 0.3 μg/ml. Aliquots of 100 μl of the reaction were removed at intervals and added to 25 μl 4% acetic acid, in microtitre plates, to stop the reaction. At the completion of the time course the plates are read on a microplate reader at a wavelength of 405 nm. No attempt was made to quantify plasmin generation in this assay.

---

We claim:

1. A proteinaceous compound which is activatable by thrombin or Factor Xa enzyme to have fibrinolytic activity; characterized in that the compound is a plasminogen analogue, wherein the cleavage site Pro(559) to Val(562) of native plasminogen is altered by substitution of an amino acid sequence cleavable by thrombin or Factor Xa, said plasminogen analogue being activatable by thrombin or Factor Xa cleavage to have plasmin activity.

2. A compound as claimed in claim 1, wherein the enzyme is Factor Xa.

3. A compound as claimed in claim 2, wherein the amino acid sequence comprises the sequence P4-P3-Gly-Arg, wherein P4 represents a hydrophobic residue and P3 represents an acidic residue.

4. A compound as claimed in claim 3, wherein the hydrophobic residue is isoleucine.

5. A compound as claimed in claim 1, wherein the enzyme is thrombin.

6. A compound as claimed in claim 5, wherein the amino acid sequence comprises the sequence P4-P3-Pro-Arg-P1'-P2', wherein each of P4 and P3 independently represents a hydrophobic residue and each of P1' and P2' independently represents a non-acidic residue.

7. A compound as claimed in claim 5, wherein the amino acid sequence comprises the sequence P2-Arg-P1', wherein one of the residues P2 and P1' represents glycine, and the other is any amino acid residue.

8. A compound as claimed in claim 5, wherein the amino acid sequence comprises the sequence Gly-Pro-Arg.

9. A compound as claimed in claim 1 having one or more amino acid substitutions, additions or deletions between residues Pro(555) and Cys(566) inclusive.

10. A plasminogen analogue as claimed in claim 1 wherein the cleavage site sequence (SEQ ID NO:6) is:

Pro Lys Lys Cys Ile Glu Gly Arg Val Val Gly Gly Cys
1            5                    10 and is in a position corresponding to that of the cleavage site sequence from Pro(555) to Cys(566) inclusive of wild-type plasminogen.

11. A plasminogen analogue as claimed in claim 1 wherein the cleavage site sequence (SEQ ID NO:8) is:

Pro Lys Lys Cys Gly Ile Glu Gly Arg Val Val Gly Gly Cys
1            5                    10 and is in a position corresponding to that of the cleavage site sequence from Pro(555) to Cys(566) inclusive of wild-type plasminogen.

12. A plasminogen analogue as claimed in claim 1 wherein the cleavage site sequence (SEQ ID NO:10) is:

Pro Lys Lys Cys Gly Ala Ile Glu Gly Arg Val Val Gly Gly Cys
1            5                    10                   15 and is in a position corresponding to that of the cleavage site sequence from Pro(555) to Cys(566) inclusive of wild-type plasminogen.

13. A plasminogen analogue as claimed in claim 1 wherein the cleavage site sequence (SEQ ID NO:12) is:

Pro Lys Lys Cys Gly Tyr Ile Asp Gly Arg Val Val Gly Gly Cys
1            5                    10                   15 and is in a position corresponding to that of the cleavage site sequence from Pro(555) to Cys(566) inclusive of wild-type plasminogen.

14. A plasminogen analogue as claimed in claim 1 wherein the cleavage site sequence (SEQ ID NO:14) is:

Pro Lys Lys Cys Gly Tyr Ile Asp Gly Arg Ile Val Gly Gly Cys
1            5                    10                   15 and is in a position corresponding to that of the cleavage site sequence from Pro(555) to Cys (566) inclusive of wild-type plasminogen.

15. A plasminogen analogue as claimed in claim 1 wherein the cleavage site sequence (SEQ ID NO:18) is:

Val Glu Pro Lys Lys Cys Gly Pro Arg Val Val Gly Gly Cys
1            5                    10 and is in a position corresponding to that of the cleavage site sequence from Val(553) to Cys (566) inclusive of wild-type plasminogen.

16. A plasminogen analogue as claimed in claim 1 wherein the cleavage site sequence (SEQ ID NO:20) is:

Val Glu Pro Lys Lys Cys Gly Gly Pro Arg Val Val Gly Gly Cys
1            5                    10                   15 and is in a position corresponding to that of the cleavage site sequence from Val(553) to Cys(566) inclusive of wild-type plasminogen.

17. A plasminogen analogue as claimed in claim 1 wherein the cleavage site sequence (SEQ ID NO:28) is:

Val Glu Pro Lys Lys Cys Val Val Pro Arg Val Val Gly Gly Cys
1            5                    10                   15 and is in a position corresponding to that of the cleavage site sequence from Val(553) to Cys(566) inclusive of wild-type plasminogen.

18. A plasminogen analogue as claimed in claim 1 wherein the cleavage site sequence (SEQ ID NO:32) is:

Val Glu Pro Lys Lys Cys Pro Ser Gly Arg Val Val Gly Gly Cys
1            5                    10                   15 and is in a position corresponding to that of the cleavage site sequence from Val(553) to Cys(566) inclusive of wild-type plasminogen.

19. A plasminogen analogue as claimed in claim 1 wherein the cleavage site sequence (SEQ ID NO:34) is:

Val Glu Pro Lys Lys Cys Val Glu Leu Gln Gly Val Val Pro Arg
1            5                    10                   15
Val Val Gly Gly Cys
              20 and is in a position corresponding to that of the cleavage site sequence from Val(553) to Cys(566) inclusive of wild-type plasminogen.

20. A proteinaceous compound which is activatable by Factor Xa to have fibrinolytic activity; characterized in that the compound is a plasminogen analogue, wherein the cleavage site Pro(559) to Val(562) of native plasminogen is altered by substitution of an amino acid sequence clearable by Factor Xa; said amino acid sequence comprising a sequence P4-P3-Gly-Arg, wherein P4 represents a hydrophobic residue and P3 represents an acidic residue; said plasminogen analogue being activatable by Factor Xa cleavage to have plasmin activity.

21. A compound as claimed claim 20, wherein the hydrophobic residue is isoleucine.

22. A proteinaceous compound which is activatable by thrombin to have fibrinolytic activity; characterized in that the compound is a plasminogen analogue, wherein the cleavage site Pro(559) to Val(562) of native plasminogen is altered by substitution of an amino acid sequence clearable by thrombin; said amino acid sequence comprising a sequence P4-P3-Pro-Arg-P1'-P2', wherein each of P4 and P3 independently represents a hydrophobic residue and each of P1' and P2' independently represents a non-acidic residue; said plasminogen analogue being activatable by thrombin cleavage to have plasmin activity.

23. A proteinaceous compound which is activatable by thrombin to have fibrinolytic activity; characterized in that the compound is a plasminogen analogue, wherein the cleavage site Pro(559) to Val(562) of native plasminogen is altered by substitution of an amino acid sequence clearable by thrombin; said amino acid sequence comprising a sequence P2-Arg-P1', wherein one of the residues P2 and P1' represents glycine and the other represents any amino acid residue; said plasminogen analogue being activatable by thrombin cleavage to have plasmin activity.

24. A proteinaceous compound which is activatable by thrombin to have fibrinolytic activity; characterized in that the compound is a plasminogen analogue, wherein the cleavage site Pro(559) to Val(562) of native plasminogen is altered by substitution of an amino acid sequence clearable by thrombin; said amino acid sequence comprising a sequence Gly-Pro-Arg; said plasminogen analogue being activatable by thrombin cleavage to have plasmin activity.

* * * * *

SEQUENCE LISTING ( 1 ) GENERAL INFORMATION:

( i i i ) NUMBER OF SEQUENCES: 67

( 2 ) INFORMATION FOR SEQ ID NO:1:

( i ) SEQUENCE CHARACTERISTICS:
        ( A ) LENGTH: 2753 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..2753
        ( D ) OTHER INFORMATION: /note="FIG. 2 Plasminogen cDNA sequence"

( i x ) FEATURE:
        ( A ) NAME/KEY: sig_peptide
        ( B ) LOCATION: 65..121

( i x ) FEATURE:
        ( A ) NAME/KEY: mat_peptide
        ( B ) LOCATION: 122..2494

( i x ) FEATURE:
        ( A ) NAME/KEY: CDS
        ( B ) LOCATION: 65..2494

( i x ) FEATURE:
        ( A ) NAME/KEY: misc_feature
        ( B ) LOCATION: 54..55
        ( D ) OTHER INFORMATION: /note="BalI site"

( i x ) FEATURE:
        ( A ) NAME/KEY: misc_feature
        ( B ) LOCATION: 2564..2565
        ( D ) OTHER INFORMATION: /note="SphI site"

( x i ) SEQUENCE DESCRIPTION: SEQ ID NO:1:

```
GATGTAAGTC  AACAACATCC  TGGGATTGGG  ACCCACTTTC  TGGGCACTGC  TGGCCAGTCC                          60

CAAA ATG GAA CAT AAG GAA GTG GTT CTT CTA CTT CTT TTA TTT CTG AAA                              109
     Met Glu His Lys Glu Val Val Leu Leu Leu Leu Leu Phe Leu Lys
     -19         -15              -10                  -5
```

| | | | | | | | | | | | | | | | | |
|---|---|---|---|---|---|---|---|---|---|---|---|---|---|---|---|---|
|TCA|GGT|CAA|GGA|GAG|CCT|CTG|GAT|GAC|TAT|GTG|AAT|ACC|CAG|GGG|GCT|157|
|Ser|Gly|Gln|Gly|Glu|Pro|Leu|Asp|Asp|Tyr|Val|Asn|Thr|Gln|Gly|Ala||
| | |  |1| | | |  |5| | | | |  |10| | |
|TCA|CTG|TTC|AGT|GTC|ACT|AAG|AAG|CAG|CTG|GGA|GCA|GGA|AGT|ATA|GAA|205|
|Ser|Leu|Phe|Ser|Val|Thr|Lys|Lys|Gln|Leu|Gly|Ala|Gly|Ser|Ile|Glu||
| | |15| | | | |20| | | | |  |25| | | |
|GAA|TGT|GCA|GCA|AAA|TGT|GAG|GAG|GAC|GAA|GAA|TTC|ACC|TGC|AGG|GCA|253|
|Glu|Cys|Ala|Ala|Lys|Cys|Glu|Glu|Asp|Glu|Glu|Phe|Thr|Cys|Arg|Ala||
| | |30| | | | |35| | | | |40| | | | |
|TTC|CAA|TAT|CAC|AGT|AAA|GAG|CAA|CAA|TGT|GTG|ATA|ATG|GCT|GAA|AAC|301|
|Phe|Gln|Tyr|His|Ser|Lys|Glu|Gln|Gln|Cys|Val|Ile|Met|Ala|Glu|Asn||
|45| | | | |50| | | | |55| | | | |60| |
|AGG|AAG|TCC|TCC|ATA|ATC|ATT|AGG|ATG|AGA|GAT|GTA|GTT|TTA|TTT|GAA|349|
|Arg|Lys|Ser|Ser|Ile|Ile|Ile|Arg|Met|Arg|Asp|Val|Val|Leu|Phe|Glu||
| | | | |65| | | | |70| | | | |75| | |
|AAG|AAA|GTG|TAT|CTC|TCA|GAG|TGC|AAG|ACT|GGG|AAT|GGA|AAG|AAC|TAC|397|
|Lys|Lys|Val|Tyr|Leu|Ser|Glu|Cys|Lys|Thr|Gly|Asn|Gly|Lys|Asn|Tyr||
| | | |80| | | | |85| | | | |90| | | |
|AGA|GGG|ACG|ATG|TCC|AAA|ACA|AAA|AAT|GGC|ATC|ACC|TGT|CAA|AAA|TGG|445|
|Arg|Gly|Thr|Met|Ser|Lys|Thr|Lys|Asn|Gly|Ile|Thr|Cys|Gln|Lys|Trp||
| | |95| | | | |100| | | | |105| | | | |
|AGT|TCC|ACT|TCT|CCC|CAC|AGA|CCT|AGA|TTC|TCA|CCT|GCT|ACA|CAC|CCC|493|
|Ser|Ser|Thr|Ser|Pro|His|Arg|Pro|Arg|Phe|Ser|Pro|Ala|Thr|His|Pro||
| | |110| | | | |115| | | | |120| | | | |
|TCA|GAG|GGA|CTG|GAG|GAG|AAC|TAC|TGC|AGG|AAT|CCA|GAC|AAC|GAT|CCG|541|
|Ser|Glu|Gly|Leu|Glu|Glu|Asn|Tyr|Cys|Arg|Asn|Pro|Asp|Asn|Asp|Pro||
|125| | | | |130| | | | |135| | | | |140| |
|CAG|GGG|CCC|TGG|TGC|TAT|ACT|ACT|GAT|CCA|GAA|AAG|AGA|TAT|GAC|TAC|589|
|Gln|Gly|Pro|Trp|Cys|Tyr|Thr|Thr|Asp|Pro|Glu|Lys|Arg|Tyr|Asp|Tyr||
| | | | |145| | | | |150| | | | |155| | |
|TGC|GAC|ATT|CTT|GAG|TGT|GAA|GAG|GAA|TGT|ATG|CAT|TGC|AGT|GGA|GAA|637|
|Cys|Asp|Ile|Leu|Glu|Cys|Glu|Glu|Glu|Cys|Met|His|Cys|Ser|Gly|Glu||
| | | |160| | | | |165| | | | |170| | | |
|AAC|TAT|GAC|GGC|AAA|ATT|TCC|AAG|ACC|ATG|TCT|GGA|CTG|GAA|TGC|CAG|685|
|Asn|Tyr|Asp|Gly|Lys|Ile|Ser|Lys|Thr|Met|Ser|Gly|Leu|Glu|Cys|Gln||
| | |175| | | | |180| | | | |185| | | | |
|GCC|TGG|GAC|TCT|CAG|AGC|CCA|CAC|GCT|CAT|GGA|TAC|ATT|CCT|TCC|AAA|733|
|Ala|Trp|Asp|Ser|Gln|Ser|Pro|His|Ala|His|Gly|Tyr|Ile|Pro|Ser|Lys||
| | |190| | | | |195| | | | |200| | | | |
|TTT|CCA|AAC|AAG|AAC|CTG|AAG|AAG|AAT|TAC|TGT|CGT|AAC|CCC|GAT|AGG|781|
|Phe|Pro|Asn|Lys|Asn|Leu|Lys|Lys|Asn|Tyr|Cys|Arg|Asn|Pro|Asp|Arg||
|205| | | | |210| | | | |215| | | | |220| |
|GAG|CTG|CGG|CCT|TGG|TGT|TTC|ACC|ACC|GAC|CCC|AAC|AAG|CGC|TGG|GAA|829|
|Glu|Leu|Arg|Pro|Trp|Cys|Phe|Thr|Thr|Asp|Pro|Asn|Lys|Arg|Trp|Glu||
| | | | |225| | | | |230| | | | |235| | |
|CTT|TGC|GAC|ATC|CCC|CGC|TGC|ACA|ACA|CCT|CCA|CCA|TCT|TCT|GGT|CCC|877|
|Leu|Cys|Asp|Ile|Pro|Arg|Cys|Thr|Thr|Pro|Pro|Pro|Ser|Ser|Gly|Pro||
| | | |240| | | | |245| | | | |250| | | |
|ACC|TAC|CAG|TGT|CTG|AAG|GGA|ACA|GGT|GAA|AAC|TAT|CGC|GGG|AAT|GTG|925|
|Thr|Tyr|Gln|Cys|Leu|Lys|Gly|Thr|Gly|Glu|Asn|Tyr|Arg|Gly|Asn|Val||
| | |255| | | | |260| | | | |265| | | | |
|GCT|GTT|ACC|GTG|TCC|GGG|CAC|ACC|TGT|CAG|CAC|TGG|AGT|GCA|CAG|ACC|973|
|Ala|Val|Thr|Val|Ser|Gly|His|Thr|Cys|Gln|His|Trp|Ser|Ala|Gln|Thr||
| | |270| | | | |275| | | | |280| | | | |
|CCT|CAC|ACA|CAT|AAC|AGG|ACA|CCA|GAA|AAC|TTT|CCC|TGC|AAA|AAT|TTG|1021|
|Pro|His|Thr|His|Asn|Arg|Thr|Pro|Glu|Asn|Phe|Pro|Cys|Lys|Asn|Leu||
|285| | | | |290| | | | |295| | | | |300| |
|GAT|GAA|AAC|TAC|TGC|CGC|AAT|CCT|GAC|GGA|AAA|AGG|GCC|CCA|TGG|TGC|1069|
|Asp|Glu|Asn|Tyr|Cys|Arg|Asn|Pro|Asp|Gly|Lys|Arg|Ala|Pro|Trp|Cys||
| | | | |305| | | | |310| | | | |315| | |

```
CAT ACA ACC AAC AGC CAA GTG CGG TGG GAG TAC TGT AAG ATA CCG TCC       1117
His Thr Thr Asn Ser Gln Val Arg Trp Glu Tyr Cys Lys Ile Pro Ser
            320             325                 330

TGT GAC TCC TCC CCA GTA TCC ACG GAA CAA TTG GCT CCC ACA GCA CCA       1165
Cys Asp Ser Ser Pro Val Ser Thr Glu Gln Leu Ala Pro Thr Ala Pro
        335             340                 345

CCT GAG CTA ACC CCT GTG GTC CAG GAC TGC TAC CAT GGT GAT GGA CAG       1213
Pro Glu Leu Thr Pro Val Val Gln Asp Cys Tyr His Gly Asp Gly Gln
    350             355                 360

AGC TAC CGA GGC ACA TCC TCC ACC ACC ACC ACA GGA AAG AAG TGT CAG       1261
Ser Tyr Arg Gly Thr Ser Ser Thr Thr Thr Thr Gly Lys Lys Cys Gln
365             370             375                 380

TCT TGG TCA TCT ATG ACA CCA CAC CGG CAC CAG AAG ACC CCA GAA AAC       1309
Ser Trp Ser Ser Met Thr Pro His Arg His Gln Lys Thr Pro Glu Asn
                385             390                 395

TAC CCA AAT GCT GGC CTG ACA ATG AAC TAC TGC AGG AAT CCA GAT GCC       1357
Tyr Pro Asn Ala Gly Leu Thr Met Asn Tyr Cys Arg Asn Pro Asp Ala
            400             405                 410

GAT AAA GGC CCC TGG TGT TTT ACC ACA GAC CCC AGC GTC AGG TGG GAG       1405
Asp Lys Gly Pro Trp Cys Phe Thr Thr Asp Pro Ser Val Arg Trp Glu
        415             420                 425

TAC TGC AAC CTG AAA AAA TGC TCA GGA ACA GAA GCG AGT GTT GTA GCA       1453
Tyr Cys Asn Leu Lys Lys Cys Ser Gly Thr Glu Ala Ser Val Val Ala
    430             435                 440

CCT CCG CCT GTT GTC CTG CTT CCA GAT GTA GAG ACT CCT TCC GAA GAA       1501
Pro Pro Pro Val Val Leu Leu Pro Asp Val Glu Thr Pro Ser Glu Glu
445             450                 455                 460

GAC TGT ATG TTT GGG AAT GGG AAA GGA TAC CGA GGC AAG AGG GCG ACC       1549
Asp Cys Met Phe Gly Asn Gly Lys Gly Tyr Arg Gly Lys Arg Ala Thr
                465             470                 475

ACT GTT ACT GGG ACG CCA TGC CAG GAC TGG GCT GCC CAG GAG CCC CAT       1597
Thr Val Thr Gly Thr Pro Cys Gln Asp Trp Ala Ala Gln Glu Pro His
            480             485                 490

AGA CAC AGC ATT TTC ACT CCA GAG ACA AAT CCA CGG GCG GGT CTG GAA       1645
Arg His Ser Ile Phe Thr Pro Glu Thr Asn Pro Arg Ala Gly Leu Glu
        495             500                 505

AAA AAT TAC TGC CGT AAC CCT GAT GGT GAT GTA GGT GGT CCC TGG TGC       1693
Lys Asn Tyr Cys Arg Asn Pro Asp Gly Asp Val Gly Gly Pro Trp Cys
    510             515                 520

TAC ACG ACA AAT CCA AGA AAA CTT TAC GAC TAC TGT GAT GTC CCT CAG       1741
Tyr Thr Thr Asn Pro Arg Lys Leu Tyr Asp Tyr Cys Asp Val Pro Gln
525             530                 535                 540

TGT GCG GCC CCT TCA TTT GAT TGT GGG AAG CCT CAA GTG GAG CCG AAG       1789
Cys Ala Ala Pro Ser Phe Asp Cys Gly Lys Pro Gln Val Glu Pro Lys
                545             550                 555

AAA TGT CCT GGA AGG GTT GTA GGG GGG TGT GTG GCC CAC CCA CAT TCC       1837
Lys Cys Pro Gly Arg Val Val Gly Gly Cys Val Ala His Pro His Ser
            560             565                 570

TGG CCC TGG CAA GTC AGT CTT AGA ACA AGG TTT GGA ATG CAC TTC TGT       1885
Trp Pro Trp Gln Val Ser Leu Arg Thr Arg Phe Gly Met His Phe Cys
        575             580                 585

GGA GGC ACC TTG ATA TCC CCA GAG TGG GTG TTG ACT GCT GCC CAC TGC       1933
Gly Gly Thr Leu Ile Ser Pro Glu Trp Val Leu Thr Ala Ala His Cys
    590             595                 600

TTG GAG AAG TCC CCA AGG CCT TCA TCC TAC AAG GTC ATC CTG GGT GCA       1981
Leu Glu Lys Ser Pro Arg Pro Ser Ser Tyr Lys Val Ile Leu Gly Ala
605             610                 615                 620

CAC CAA GAA GTG AAT CTC GAA CCG CAT GTT CAG GAA ATA GAA GTG TCT       2029
His Gln Glu Val Asn Leu Glu Pro His Val Gln Glu Ile Glu Val Ser
                625             630                 635
```

| | | | | | | | | | | | | | | | | |
|---|---|---|---|---|---|---|---|---|---|---|---|---|---|---|---|---|
| AGG | CTG | TTC | TTG | GAG | CCC | ACA | CGA | AAA | GAT | ATT | GCC | TTG | CTA | AAG | CTA | 2077 |
| Arg | Leu | Phe | Leu | Glu | Pro | Thr | Arg | Lys | Asp | Ile | Ala | Leu | Leu | Lys | Leu | |
| | | | 640 | | | | 645 | | | | | | 650 | | | |
| AGC | AGT | CCT | GCC | GTC | ATC | ACT | GAC | AAA | GTA | ATC | CCA | GCT | TGT | CTG | CCA | 2125 |
| Ser | Ser | Pro | Ala | Val | Ile | Thr | Asp | Lys | Val | Ile | Pro | Ala | Cys | Leu | Pro | |
| | | 655 | | | | | 660 | | | | | 665 | | | | |
| TCC | CCA | AAT | TAT | GTG | GTC | GCT | GAC | CGG | ACC | GAA | TGT | TTC | ATC | ACT | GGC | 2173 |
| Ser | Pro | Asn | Tyr | Val | Val | Ala | Asp | Arg | Thr | Glu | Cys | Phe | Ile | Thr | Gly | |
| | 670 | | | | | 675 | | | | | 680 | | | | | |
| TGG | GGA | GAA | ACC | CAA | GGT | ACT | TTT | GGA | GCT | GGC | CTT | CTC | AAG | GAA | GCC | 2221 |
| Trp | Gly | Glu | Thr | Gln | Gly | Thr | Phe | Gly | Ala | Gly | Leu | Leu | Lys | Glu | Ala | |
| 685 | | | | 690 | | | | | 695 | | | | | 700 | | |
| CAG | CTC | CCT | GTG | ATT | GAG | AAT | AAA | GTG | TGC | AAT | CGC | TAT | GAG | TTT | CTG | 2269 |
| Gln | Leu | Pro | Val | Ile | Glu | Asn | Lys | Val | Cys | Asn | Arg | Tyr | Glu | Phe | Leu | |
| | | | | 705 | | | | 710 | | | | | 715 | | | |
| AAT | GGA | AGA | GTC | CAA | TCC | ACC | GAA | CTC | TGT | GCT | GGG | CAT | TTG | GCC | GGA | 2317 |
| Asn | Gly | Arg | Val | Gln | Ser | Thr | Glu | Leu | Cys | Ala | Gly | His | Leu | Ala | Gly | |
| | | | 720 | | | | 725 | | | | | 730 | | | | |
| GGC | ACT | GAC | AGT | TGC | CAG | GGT | GAC | AGT | GGA | GGT | CCT | CTG | GTT | TGC | TTC | 2365 |
| Gly | Thr | Asp | Ser | Cys | Gln | Gly | Asp | Ser | Gly | Gly | Pro | Leu | Val | Cys | Phe | |
| | | 735 | | | | 740 | | | | | 745 | | | | | |
| GAG | AAG | GAC | AAA | TAC | ATT | TTA | CAA | GGA | GTC | ACT | TCT | TGG | GGT | CTT | GGC | 2413 |
| Glu | Lys | Asp | Lys | Tyr | Ile | Leu | Gln | Gly | Val | Thr | Ser | Trp | Gly | Leu | Gly | |
| | 750 | | | | | 755 | | | | | 760 | | | | | |
| TGT | GCA | CGC | CCC | AAT | AAG | CCT | GGT | GTC | TAT | GTT | CGT | GTT | TCA | AGG | TTT | 2461 |
| Cys | Ala | Arg | Pro | Asn | Lys | Pro | Gly | Val | Tyr | Val | Arg | Val | Ser | Arg | Phe | |
| 765 | | | | | 770 | | | | | 775 | | | | | 780 | |
| GTT | ACT | TGG | ATT | GAG | GGA | GTG | ATG | AGA | AAT | AAT | TAATTGGACG | | GGAGACAGAG | | | 2514 |
| Val | Thr | Trp | Ile | Glu | Gly | Val | Met | Arg | Asn | Asn | | | | | | |
| | | | | 785 | | | | | 790 | | | | | | | |

TGACGCACTG ACTCACCTAG AGGCTGGAAC GTGGGTAGGG ATTTAGCATG CTGGAAATAA 2574

CTGGCAGTAA TCAAACGAAG ACACTGTCCC CAGCTACCAG CTACGCCAAA CCTCGGCATT 2634

TTTTGTGTTA TTTTCTGACT GCTGGATTCT GTAGTAAGGT GACATAGCTA TGACATTTGT 2694

TAAAAATAAA CTCTGTACTT AACTTTGATT TGAGTAAATT TTGGTTTTGG TCTTCAACA 2753

( 2 ) INFORMATION FOR SEQ ID NO:2:

( i ) SEQUENCE CHARACTERISTICS:
        ( A ) LENGTH: 810 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Glu | His | Lys | Glu | Val | Val | Leu | Leu | Leu | Leu | Phe | Leu | Lys | Ser |
| -19 | | | | -15 | | | | | -10 | | | | | -5 |
| Gly | Gln | Gly | Glu | Pro | Leu | Asp | Asp | Tyr | Val | Asn | Thr | Gln | Gly | Ala | Ser |
| | | | | 1 | | | | 5 | | | | | 10 | | |
| Leu | Phe | Ser | Val | Thr | Lys | Lys | Gln | Leu | Gly | Ala | Gly | Ser | Ile | Glu | Glu |
| | | 15 | | | | 20 | | | | | 25 | | | | |
| Cys | Ala | Ala | Lys | Cys | Glu | Glu | Asp | Glu | Glu | Phe | Thr | Cys | Arg | Ala | Phe |
| 30 | | | | | 35 | | | | | 40 | | | | | 45 |
| Gln | Tyr | His | Ser | Lys | Glu | Gln | Gln | Cys | Val | Ile | Met | Ala | Glu | Asn | Arg |
| | | | | 50 | | | | | 55 | | | | | 60 | |
| Lys | Ser | Ser | Ile | Ile | Ile | Arg | Met | Arg | Asp | Val | Val | Leu | Phe | Glu | Lys |
| | | | | 65 | | | | | 70 | | | | | 75 | |
| Lys | Val | Tyr | Leu | Ser | Glu | Cys | Lys | Thr | Gly | Asn | Gly | Lys | Asn | Tyr | Arg |

|     |     |     |     |     | 80  |     |     |     |     | 85  |     |     |     |     | 90  |     |     |     |     |
| --- | --- | --- | --- | --- | --- | --- | --- | --- | --- | --- | --- | --- | --- | --- | --- | --- | --- | --- | --- |

Gly Thr Met Ser Lys Thr Lys Asn Gly Ile Thr Cys Gln Lys Trp Ser
    95                        100                    105

Ser Thr Ser Pro His Arg Pro Arg Phe Ser Pro Ala Thr His Pro Ser
110                  115                  120                  125

Glu Gly Leu Glu Glu Asn Tyr Cys Arg Asn Pro Asp Asn Asp Pro Gln
                  130                  135                  140

Gly Pro Trp Cys Tyr Thr Thr Asp Pro Glu Lys Arg Tyr Asp Tyr Cys
            145                  150                  155

Asp Ile Leu Glu Cys Glu Glu Cys Met His Cys Ser Gly Glu Asn
          160                  165                170

Tyr Asp Gly Lys Ile Ser Lys Thr Met Ser Gly Leu Glu Cys Gln Ala
    175                    180                185

Trp Asp Ser Gln Ser Pro His Ala His Gly Tyr Ile Pro Ser Lys Phe
190                  195                  200                205

Pro Asn Lys Asn Leu Lys Lys Asn Tyr Cys Arg Asn Pro Asp Arg Glu
                  210                  215                  220

Leu Arg Pro Trp Cys Phe Thr Thr Asp Pro Asn Lys Arg Trp Glu Leu
            225                  230                  235

Cys Asp Ile Pro Arg Cys Thr Thr Pro Pro Pro Ser Ser Gly Pro Thr
          240                  245                250

Tyr Gln Cys Leu Lys Gly Thr Gly Glu Asn Tyr Arg Gly Asn Val Ala
    255                    260                265

Val Thr Val Ser Gly His Thr Cys Gln His Trp Ser Ala Gln Thr Pro
270                  275                  280                285

His Thr His Asn Arg Thr Pro Glu Asn Phe Pro Cys Lys Asn Leu Asp
                  290                  295                  300

Glu Asn Tyr Cys Arg Asn Pro Asp Gly Lys Arg Ala Pro Trp Cys His
            305                  310                  315

Thr Thr Asn Ser Gln Val Arg Trp Glu Tyr Cys Lys Ile Pro Ser Cys
          320                  325                330

Asp Ser Ser Pro Val Ser Thr Glu Gln Leu Ala Pro Thr Ala Pro Pro
    335                    340                345

Glu Leu Thr Pro Val Val Gln Asp Cys Tyr His Gly Asp Gly Gln Ser
350                  355                  360                365

Tyr Arg Gly Thr Ser Ser Thr Thr Thr Thr Gly Lys Lys Cys Gln Ser
            370                  375                  380

Trp Ser Ser Met Thr Pro His Arg His Gln Lys Thr Pro Glu Asn Tyr
            385                  390                  395

Pro Asn Ala Gly Leu Thr Met Asn Tyr Cys Arg Asn Pro Asp Ala Asp
          400                  405                410

Lys Gly Pro Trp Cys Phe Thr Thr Asp Pro Ser Val Arg Trp Glu Tyr
    415                    420                425

Cys Asn Leu Lys Lys Cys Ser Gly Thr Glu Ala Ser Val Val Ala Pro
430                  435                  440                445

Pro Pro Val Val Leu Leu Pro Asp Val Glu Thr Pro Ser Glu Glu Asp
                  450                  455                  460

Cys Met Phe Gly Asn Gly Lys Gly Tyr Arg Gly Lys Arg Ala Thr Thr
            465                  470                475

Val Thr Gly Thr Pro Cys Gln Asp Trp Ala Ala Gln Glu Pro His Arg
          480                  485                490

His Ser Ile Phe Thr Pro Glu Thr Asn Pro Arg Ala Gly Leu Glu Lys
    495                    500                505

| | | | | | | | | | | | | | |
|---|---|---|---|---|---|---|---|---|---|---|---|---|---|
| Asn<br>510 | Tyr | Cys | Arg | Asn | Pro<br>515 | Asp | Gly | Asp | Val<br>520 | Gly | Pro | Trp | Cys | Tyr<br>525 |
| Thr | Thr | Asn | Pro | Arg<br>530 | Lys | Leu | Tyr | Asp<br>535 | Tyr | Cys | Asp | Val | Pro | Gln<br>540 | Cys |
| Ala | Ala | Pro | Ser<br>545 | Phe | Asp | Cys | Gly | Lys<br>550 | Pro | Gln | Val | Glu | Pro<br>555 | Lys | Lys |
| Cys | Pro | Gly<br>560 | Arg | Val | Val | Gly | Gly<br>565 | Cys | Val | Ala | His | Pro<br>570 | His | Ser | Trp |
| Pro | Trp<br>575 | Gln | Val | Ser | Leu | Arg<br>580 | Thr | Arg | Phe | Gly | Met<br>585 | His | Phe | Cys | Gly |
| Gly<br>590 | Thr | Leu | Ile | Ser | Pro<br>595 | Glu | Trp | Val | Leu | Thr<br>600 | Ala | Ala | His | Cys | Leu<br>605 |
| Glu | Lys | Ser | Pro | Arg<br>610 | Pro | Ser | Ser | Tyr | Lys<br>615 | Val | Ile | Leu | Gly | Ala<br>620 | His |
| Gln | Glu | Val | Asn<br>625 | Leu | Glu | Pro | His | Val<br>630 | Gln | Glu | Ile | Glu | Val<br>635 | Ser | Arg |
| Leu | Phe | Leu<br>640 | Glu | Pro | Thr | Arg | Lys<br>645 | Asp | Ile | Ala | Leu | Leu<br>650 | Lys | Leu | Ser |
| Ser | Pro<br>655 | Ala | Val | Ile | Thr | Asp<br>660 | Lys | Val | Ile | Pro | Ala<br>665 | Cys | Leu | Pro | Ser |
| Pro<br>670 | Asn | Tyr | Val | Val | Ala<br>675 | Asp | Arg | Thr | Glu | Cys<br>680 | Phe | Ile | Thr | Gly | Trp<br>685 |
| Gly | Glu | Thr | Gln | Gly<br>690 | Thr | Phe | Gly | Ala | Gly<br>695 | Leu | Leu | Lys | Glu | Ala<br>700 | Gln |
| Leu | Pro | Val | Ile<br>705 | Glu | Asn | Lys | Val | Cys<br>710 | Asn | Arg | Tyr | Glu | Phe<br>715 | Leu | Asn |
| Gly | Arg | Val<br>720 | Gln | Ser | Thr | Glu | Leu<br>725 | Cys | Ala | Gly | His | Leu<br>730 | Ala | Gly | Gly |
| Thr | Asp<br>735 | Ser | Cys | Gln | Gly | Asp<br>740 | Ser | Gly | Gly | Pro | Leu<br>745 | Val | Cys | Phe | Glu |
| Lys<br>750 | Asp | Lys | Tyr | Ile | Leu<br>755 | Gln | Gly | Val | Thr | Ser<br>760 | Trp | Gly | Leu | Gly | Cys<br>765 |
| Ala | Arg | Pro | Asn | Lys<br>770 | Pro | Gly | Val | Tyr | Val<br>775 | Arg | Val | Ser | Arg | Phe<br>780 | Val |
| Thr | Trp | Ile | Glu<br>785 | Gly | Val | Met | Arg | Asn<br>790 | Asn | | | | | | |

( 2 ) INFORMATION FOR SEQ ID NO:3:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..36
        ( D ) OTHER INFORMATION: /note="Fig 4 WT cleavage site
        sequence, Factor Xa series, residues are 555-566"

( i x ) FEATURE:
        ( A ) NAME/KEY: CDS
        ( B ) LOCATION: 1..36

( i x ) FEATURE:
        ( A ) NAME/KEY: mat_peptide
        ( B ) LOCATION: 1..36

( x i ) SEQUENCE DESCRIPTION: SEQ ID NO:3:

```
CCG  AAG  AAA  TGT  CCT  GGA  AGG  GTT  GTG  GGG  GGG  TGT         36
Pro  Lys  Lys  Cys  Pro  Gly  Arg  Val  Val  Gly  Gly  Cys
 1                  5                        10
```

( 2 ) INFORMATION FOR SEQ ID NO:4:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Pro  Lys  Lys  Cys  Pro  Gly  Arg  Val  Val  Gly  Gly  Cys
 1                  5                        10
```

( 2 ) INFORMATION FOR SEQ ID NO:5:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..39
        ( D ) OTHER INFORMATION: /note="Fig 4 X1 analog"

( i x ) FEATURE:
        ( A ) NAME/KEY: CDS
        ( B ) LOCATION: 1..39

( i x ) FEATURE:
        ( A ) NAME/KEY: mat_peptide
        ( B ) LOCATION: 1..39

( x i ) SEQUENCE DESCRIPTION: SEQ ID NO:5:

```
CCG  AAG  AAA  TGT  ATC  GAG  GGA  AGG  GTT  GTG  GGG  GGG  TGT         39
Pro  Lys  Lys  Cys  Ile  Glu  Gly  Arg  Val  Val  Gly  Gly  Cys
 1                  5                        10
```

( 2 ) INFORMATION FOR SEQ ID NO:6:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Pro  Lys  Lys  Cys  Ile  Glu  Gly  Arg  Val  Val  Gly  Gly  Cys
 1                  5                        10
```

( 2 ) INFORMATION FOR SEQ ID NO:7:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..42
        ( D ) OTHER INFORMATION: /note="FIG. 4 X2 analog"

( i x ) FEATURE:
    ( A ) NAME/KEY: CDS
    ( B ) LOCATION: 1..42

( i x ) FEATURE:
    ( A ) NAME/KEY: mat_peptide
    ( B ) LOCATION: 1..42

( x i ) SEQUENCE DESCRIPTION: SEQ ID NO:7:

```
CCG AAG AAA TGT GGC ATC GAG GGA AGG GTT GTG GGG GGG TGT         42
Pro Lys Lys Cys Gly Ile Glu Gly Arg Val Val Gly Gly Cys
 1               5                  10
```

( 2 ) INFORMATION FOR SEQ ID NO:8:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Pro Lys Lys Cys Gly Ile Glu Gly Arg Val Val Gly Gly Cys
 1               5                  10
```

( 2 ) INFORMATION FOR SEQ ID NO:9:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..45
        ( D ) OTHER INFORMATION: /note="FIG. 4 X3 analog"

( x i ) SEQUENCE DESCRIPTION: SEQ ID NO:9:

```
CCG AAG AAA TGT GGT GCA ATA GAG GGA AGG GTT GTG GGG GGG TGT     45
Pro Lys Lys Cys Gly Ala Ile Glu Gly Arg Val Val Gly Gly Cys
 1               5                  10                  15
```

( 2 ) INFORMATION FOR SEQ ID NO:10:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
Pro Lys Lys Cys Gly Ala Ile Glu Gly Arg Val Val Gly Gly Cys
 1               5                  10                  15
```

( 2 ) INFORMATION FOR SEQ ID NO:11:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature ( B ) LOCATION: 1..45
( D ) OTHER INFORMATION: /note="FIG. 4 X5 analog"

( i x ) FEATURE:
( A ) NAME/KEY: CDS
( B ) LOCATION: 1..45

( i x ) FEATURE:
( A ) NAME/KEY: mat_peptide
( B ) LOCATION: 1..45

( x i ) SEQUENCE DESCRIPTION: SEQ ID NO:11:

| CCG | AAG | AAA | TGT | GGT | TAC | ATA | GAC | GGA | AGG | GTT | GTG | GGG | GGG | TGT | 45 |
|-----|-----|-----|-----|-----|-----|-----|-----|-----|-----|-----|-----|-----|-----|-----|----|
| Pro | Lys | Lys | Cys | Gly | Tyr | Ile | Asp | Gly | Arg | Val | Val | Gly | Gly | Cys |    |
| 1   |     |     |     | 5   |     |     |     |     | 10  |     |     |     |     | 15  |    |

( 2 ) INFORMATION FOR SEQ ID NO:12:

( i ) SEQUENCE CHARACTERISTICS:
( A ) LENGTH: 15 amino acids
( B ) TYPE: amino acid
( D ) TOPOLOGY: linear ( i i ) MOLECULE TYPE: protein ( x i ) SEQUENCE DESCRIPTION: SEQ ID NO:12:

Pro Lys Lys Cys Gly Tyr Ile Asp Gly Arg Val Val Gly Gly Cys
1               5                   10                  15

( 2 ) INFORMATION FOR SEQ ID NO:13:

( i ) SEQUENCE CHARACTERISTICS:
( A ) LENGTH: 45 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: misc_feature
( B ) LOCATION: 1..45
( D ) OTHER INFORMATION: /note="FIG. 4 X6 analog"

( i x ) FEATURE:
( A ) NAME/KEY: CDS
( B ) LOCATION: 1..45

( i x ) FEATURE:
( A ) NAME/KEY: mat_peptide
( B ) LOCATION: 1..45

( x i ) SEQUENCE DESCRIPTION: SEQ ID NO:13:

| CCG | AAG | AAA | TGT | GGT | TAC | ATA | GAC | GGA | AGG | ATT | GTG | GGG | GGG | TGT | 45 |
|-----|-----|-----|-----|-----|-----|-----|-----|-----|-----|-----|-----|-----|-----|-----|----|
| Pro | Lys | Lys | Cys | Gly | Tyr | Ile | Asp | Gly | Arg | Ile | Val | Gly | Gly | Cys |    |
| 1   |     |     |     | 5   |     |     |     |     | 10  |     |     |     |     | 15  |    |

( 2 ) INFORMATION FOR SEQ ID NO:14:

( i ) SEQUENCE CHARACTERISTICS:
( A ) LENGTH: 15 amino acids
( B ) TYPE: amino acid
( D ) TOPOLOGY: linear ( i i ) MOLECULE TYPE: protein ( x i ) SEQUENCE DESCRIPTION: SEQ ID NO:14:

Pro Lys Lys Cys Gly Tyr Ile Asp Gly Arg Ile Val Gly Gly Cys
1               5                   10                  15

( 2 ) INFORMATION FOR SEQ ID NO:15:

( i ) SEQUENCE CHARACTERISTICS:
    ( A ) LENGTH: 42 base pairs
    ( B ) TYPE: nucleic acid
    ( C ) STRANDEDNESS: single
    ( D ) TOPOLOGY: linear ( i i ) MOLECULE TYPE: cDNA ( i x ) FEATURE:
    ( A ) NAME/KEY: misc_feature
    ( B ) LOCATION: 1..42
    ( D ) OTHER INFORMATION: /note="FIG. 5 WT Cleavage site -
        Thrombin series, segment corresponds to residue
        553-566"

( i x ) FEATURE:
    ( A ) NAME/KEY: CDS
    ( B ) LOCATION: 1..42

( i x ) FEATURE:
    ( A ) NAME/KEY: mat_peptide
    ( B ) LOCATION: 1..42

( x i ) SEQUENCE DESCRIPTION: SEQ ID NO:15:

```
GTG  GAG  CCG  AAG  AAA  TGT  CCT  GGA  AGG  GTT  GTG  GGG  GGG  TGT       42
Val  Glu  Pro  Lys  Lys  Cys  Pro  Gly  Arg  Val  Val  Gly  Gly  Cys
 1                  5                            10
```

( 2 ) INFORMATION FOR SEQ ID NO:16:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

```
Val  Glu  Pro  Lys  Lys  Cys  Pro  Gly  Arg  Val  Val  Gly  Gly  Cys
 1                  5                            10
```

( 2 ) INFORMATION FOR SEQ ID NO:17:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..42
        ( D ) OTHER INFORMATION: /note="FIG. 5 T1 analog"

( i x ) FEATURE:
        ( A ) NAME/KEY: CDS
        ( B ) LOCATION: 1..42

( i x ) FEATURE:
        ( A ) NAME/KEY: mat_peptide
        ( B ) LOCATION: 1..42

( x i ) SEQUENCE DESCRIPTION: SEQ ID NO:17:

```
GTG  GAG  CCG  AAG  AAA  TGT  GGT  CCT  AGG  GTT  GTG  GGG  GGG  TGT       42
Val  Glu  Pro  Lys  Lys  Cys  Gly  Pro  Arg  Val  Val  Gly  Gly  Cys
 1                  5                            10
```

( 2 ) INFORMATION FOR SEQ ID NO:18:

( i ) SEQUENCE CHARACTERISTICS:
        ( A ) LENGTH: 14 amino acids
        ( B ) TYPE: amino acid (D) TOPOLOGY: linear (ii) MOLECULE TYPE: protein (xi) SEQUENCE DESCRIPTION: SEQ ID NO:18:

```
Val Glu Pro Lys Lys Cys Gly Pro Arg Val Val Gly Gly Cys
 1               5                   10
```

(2) INFORMATION FOR SEQ ID NO:19:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..45
        (D) OTHER INFORMATION: /note="FIG. 4 T2 analog"

(ix) FEATURE:
        (A) NAME/KEY: CDS
        (B) LOCATION: 1..45

(ix) FEATURE:
        (A) NAME/KEY: mat_peptide
        (B) LOCATION: 1..45

(xi) SEQUENCE DESCRIPTION: SEQ ID NO:19:

```
GTG GAG CCG AAG AAA TGT GGT GGT CCA AGG GTT GTG GGG GGG TGT      45
Val Glu Pro Lys Lys Cys Gly Gly Pro Arg Val Val Gly Gly Cys
 1               5                   10                  15
```

(2) INFORMATION FOR SEQ ID NO:20:

(i) SEQUENCE CHARACTERISTICS:
        (A) LENGTH: 15 amino acids
        (B) TYPE: amino acid
        (D) TOPOLOGY: linear (ii) MOLECULE TYPE: protein (xi) SEQUENCE DESCRIPTION: SEQ ID NO:20:

```
Val Glu Pro Lys Lys Cys Gly Gly Pro Arg Val Val Gly Gly Cys
 1               5                   10                  15
```

(2) INFORMATION FOR SEQ ID NO:21:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..48
        (D) OTHER INFORMATION: /note="FIG. 5 T6 analog"

(ix) FEATURE:
        (A) NAME/KEY: CDS
        (B) LOCATION: 1..48

(ix) FEATURE:
        (A) NAME/KEY: mat_peptide
        (B) LOCATION: 1..48

(xi) SEQUENCE DESCRIPTION: SEQ ID NO:21:

```
CTG GAG CCG GAG CTA TGT GGA GTT GTG CCT AGG GGA GTG GGG GGG TGT         48
Leu Glu Pro Glu Leu Cys Gly Val Val Pro Arg Gly Val Gly Gly Cys
 1               5                   10                  15
```

( 2 ) INFORMATION FOR SEQ ID NO:22:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: protein ( x i ) SEQUENCE DESCRIPTION: SEQ ID NO:22:

```
Leu Glu Pro Glu Leu Cys Gly Val Val Pro Arg Gly Val Gly Gly Cys
 1               5                   10                  15
```

( 2 ) INFORMATION FOR SEQ ID NO:23:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..48
        ( D ) OTHER INFORMATION: /note="FIG. 5 T7 analog"

( i x ) FEATURE:
        ( A ) NAME/KEY: CDS
        ( B ) LOCATION: 1..48

( i x ) FEATURE:
        ( A ) NAME/KEY: mat_peptide
        ( B ) LOCATION: 1..48

( x i ) SEQUENCE DESCRIPTION: SEQ ID NO:23:

```
CTG GAG CCG CAA CTA TGT GGA GTT GTG CCT AGG GGA GTG GGG GGG TGT         48
Leu Glu Pro Gln Leu Cys Gly Val Val Pro Arg Gly Val Gly Gly Cys
 1               5                   10                  15
```

( 2 ) INFORMATION FOR SEQ ID NO:24:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: protein ( x i ) SEQUENCE DESCRIPTION: SEQ ID NO:24:

```
Leu Glu Pro Gln Leu Cys Gly Val Val Pro Arg Gly Val Gly Gly Cys
 1               5                   10                  15
```

( 2 ) INFORMATION FOR SEQ ID NO:25:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..60
        ( D ) OTHER INFORMATION: /note="FIG. 5 T8 analog"

( i x ) FEATURE:
        ( A ) NAME/KEY: CDS
        ( B ) LOCATION: 1..60

( i x ) FEATURE:
        ( A ) NAME/KEY: mat_peptide
        ( B ) LOCATION: 1..60

( x i ) SEQUENCE DESCRIPTION: SEQ ID NO:25:

```
GTG GAG CCG AAG AAG TGT GTA GAA CTA CAA GGA GTA GTG CCT AGG GGA    48
Val Glu Pro Lys Lys Cys Val Glu Leu Gln Gly Val Val Pro Arg Gly
 1               5                  10                  15

GTG GGG GGG TGT                                                    60
Val Gly Gly Cys
             20
```

( 2 ) INFORMATION FOR SEQ ID NO:26:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: protein ( x i ) SEQUENCE DESCRIPTION: SEQ ID NO:26:

```
Val Glu Pro Lys Lys Cys Val Glu Leu Gln Gly Val Val Pro Arg Gly
 1               5                  10                  15

Val Gly Gly Cys
             20
```

( 2 ) INFORMATION FOR SEQ ID NO:27:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..45
        ( D ) OTHER INFORMATION: /note="FIG. 5 T13 analog"

( i x ) FEATURE:
        ( A ) NAME/KEY: CDS
        ( B ) LOCATION: 1..45

( i x ) FEATURE:
        ( A ) NAME/KEY: mat_peptide
        ( B ) LOCATION: 1..45

( x i ) SEQUENCE DESCRIPTION: SEQ ID NO:27:

```
GTG GAG CCG AAG AAA TGT GTT GTA CCT AGG GTT GTG GGG GGG TGT       45
Val Glu Pro Lys Lys Cys Val Val Pro Arg Val Val Gly Gly Cys
 1               5                  10                  15
```

( 2 ) INFORMATION FOR SEQ ID NO:28:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: protein ( x i ) SEQUENCE DESCRIPTION: SEQ ID NO:28:

```
Val Glu Pro Lys Lys Cys Val Val Pro Arg Val Val Gly Gly Cys
 1               5                  10                  15
```

(2) INFORMATION FOR SEQ ID NO:29:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..45
        (D) OTHER INFORMATION: /note="FIG. 5 T14 analog"

(ix) FEATURE:
        (A) NAME/KEY: CDS
        (B) LOCATION: 1..45

(ix) FEATURE:
        (A) NAME/KEY: mat_peptide
        (B) LOCATION: 1..45

(xi) SEQUENCE DESCRIPTION: SEQ ID NO:29:

```
GTG GAG CCG AAG AAA TGT GGA TAC CCT AGG GTT GTG GGG GGG TGT    45
Val Glu Pro Lys Lys Cys Gly Tyr Pro Arg Val Val Gly Gly Cys
 1               5                  10                   15
```

(2) INFORMATION FOR SEQ ID NO:30:

(i) SEQUENCE CHARACTERISTICS:
        (A) LENGTH: 15 amino acids
        (B) TYPE: amino acid
        (D) TOPOLOGY: linear (ii) MOLECULE TYPE: protein (xi) SEQUENCE DESCRIPTION: SEQ ID NO:30:

```
Val Glu Pro Lys Lys Cys Gly Tyr Pro Arg Val Val Gly Gly Cys
 1               5                  10                   15
```

(2) INFORMATION FOR SEQ ID NO:31:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..45
        (D) OTHER INFORMATION: /note="FIG. 5 T17 analog"

(ix) FEATURE:
        (A) NAME/KEY: CDS
        (B) LOCATION: 1..45

(ix) FEATURE:
        (A) NAME/KEY: mat_peptide
        (B) LOCATION: 1..45

(xi) SEQUENCE DESCRIPTION: SEQ ID NO:31:

```
GTG GAG CCG AAG AAA TGT CCT AGT GGA AGG GTT GTG GGG GGG TGT    45
Val Glu Pro Lys Lys Cys Pro Ser Gly Arg Val Val Gly Gly Cys
 1               5                  10                   15
```

(2) INFORMATION FOR SEQ ID NO:32:

(i) SEQUENCE CHARACTERISTICS:

( A ) LENGTH: 15 amino acids
                ( B ) TYPE: amino acid
                ( D ) TOPOLOGY: linear ( i i ) MOLECULE TYPE: protein ( x i ) SEQUENCE DESCRIPTION: SEQ ID NO:32:

```
Val Glu Pro Lys Lys Cys Pro Ser Gly Arg Val Val Gly Gly Cys
 1               5                   10                  15
```

( 2 ) INFORMATION FOR SEQ ID NO:33:

( i ) SEQUENCE CHARACTERISTICS:
                ( A ) LENGTH: 60 base pairs
                ( B ) TYPE: nucleic acid
                ( C ) STRANDEDNESS: single
                ( D ) TOPOLOGY: linear ( i i ) MOLECULE TYPE: cDNA ( i x ) FEATURE:
                ( A ) NAME/KEY: misc_feature
                ( B ) LOCATION: 1..60
                ( D ) OTHER INFORMATION: /note="FIG. 5 T19 analog"

( i x ) FEATURE:
                ( A ) NAME/KEY: CDS
                ( B ) LOCATION: 1..60

( i x ) FEATURE:
                ( A ) NAME/KEY: mat_peptide
                ( B ) LOCATION: 1..60

( x i ) SEQUENCE DESCRIPTION: SEQ ID NO:33:

```
GTG GAG CCG AAG AAA TGT GTA GAA TTG CAG GGA GTA GTC CCA AGG GTT      48
Val Glu Pro Lys Lys Cys Val Glu Leu Gln Gly Val Val Pro Arg Val
 1               5                   10                  15

GTG GGG GGG TGT                                                      60
Val Gly Gly Cys
            20
```

( 2 ) INFORMATION FOR SEQ ID NO:34:

( i ) SEQUENCE CHARACTERISTICS:
                ( A ) LENGTH: 20 amino acids
                ( B ) TYPE: amino acid
                ( D ) TOPOLOGY: linear ( i i ) MOLECULE TYPE: protein ( x i ) SEQUENCE DESCRIPTION: SEQ ID NO:34:

```
Val Glu Pro Lys Lys Cys Val Glu Leu Gln Gly Val Val Pro Arg Val
 1               5                   10                  15
Val Gly Gly Cys
            20
```

( 2 ) INFORMATION FOR SEQ ID NO:35:

( i ) SEQUENCE CHARACTERISTICS:
                ( A ) LENGTH: 54 base pairs
                ( B ) TYPE: nucleic acid
                ( C ) STRANDEDNESS: single
                ( D ) TOPOLOGY: linear ( i i ) MOLECULE TYPE: cDNA ( i x ) FEATURE:
                ( A ) NAME/KEY: misc_feature
                ( B ) LOCATION: 1..54
                ( D ) OTHER INFORMATION: /note="FIG. 5 T20 analog"

( i x ) FEATURE:

(A) NAME/KEY: CDS
        (B) LOCATION: 1..54

(ix) FEATURE:
        (A) NAME/KEY: mat_peptide
        (B) LOCATION: 1..54

(xi) SEQUENCE DESCRIPTION: SEQ ID NO:35:

| GTG | GAG | CCG | AAG | AAA | TGT | GTA | GAA | TTG | CAG | GGA | GTA | GTC | CCA | AGG | GGG | 48 |
|-----|-----|-----|-----|-----|-----|-----|-----|-----|-----|-----|-----|-----|-----|-----|-----|----|
| Val | Glu | Pro | Lys | Lys | Cys | Val | Glu | Leu | Gln | Gly | Val | Val | Pro | Arg | Gly |    |
| 1   |     |     |     | 5   |     |     |     |     | 10  |     |     |     |     | 15  |     |    |

| GGG | TGT | 54 |
|-----|-----|----|
| Gly | Cys |    |

(2) INFORMATION FOR SEQ ID NO:36:

(i) SEQUENCE CHARACTERISTICS:
        (A) LENGTH: 18 amino acids
        (B) TYPE: amino acid
        (D) TOPOLOGY: linear (ii) MOLECULE TYPE: protein (xi) SEQUENCE DESCRIPTION: SEQ ID NO:36:

| Val | Glu | Pro | Lys | Lys | Cys | Val | Glu | Leu | Gln | Gly | Val | Val | Pro | Arg | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Gly Cys (2) INFORMATION FOR SEQ ID NO:37:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..48
        (D) OTHER INFORMATION: /note="FIG. 5 T21 analog"

(ix) FEATURE:
        (A) NAME/KEY: CDS
        (B) LOCATION: 1..48

(ix) FEATURE:
        (A) NAME/KEY: mat_peptide
        (B) LOCATION: 1..48

(xi) SEQUENCE DESCRIPTION: SEQ ID NO:37:

| CTG | GAG | CCG | GAG | CTA | TGT | GGA | GTT | GTG | CCT | AGG | GTA | GTG | GGG | GGG | TGT | 48 |
|-----|-----|-----|-----|-----|-----|-----|-----|-----|-----|-----|-----|-----|-----|-----|-----|----|
| Leu | Glu | Pro | Glu | Leu | Cys | Gly | Val | Val | Pro | Arg | Val | Val | Gly | Gly | Cys |    |
| 1   |     |     |     | 5   |     |     |     |     | 10  |     |     |     |     | 15  |     |    |

(2) INFORMATION FOR SEQ ID NO:38:

(i) SEQUENCE CHARACTERISTICS:
        (A) LENGTH: 16 amino acids
        (B) TYPE: amino acid
        (D) TOPOLOGY: linear (ii) MOLECULE TYPE: protein (xi) SEQUENCE DESCRIPTION: SEQ ID NO:38:

| Leu | Glu | Pro | Glu | Leu | Cys | Gly | Val | Val | Pro | Arg | Val | Val | Gly | Gly | Cys |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

(2) INFORMATION FOR SEQ ID NO:39:

(i) SEQUENCE CHARACTERISTICS:
    (A) LENGTH: 48 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: misc_feature
    (B) LOCATION: 1..48
    (D) OTHER INFORMATION: /note="FIG. 5 T22 analog"

(ix) FEATURE:
    (A) NAME/KEY: CDS
    (B) LOCATION: 1..48

(ix) FEATURE:
    (A) NAME/KEY: mat_peptide
    (B) LOCATION: 1..48

(xi) SEQUENCE DESCRIPTION: SEQ ID NO:39:

| CTG | GAG | CCG | CAA | CTA | TGT | GGA | GTT | GTG | CCT | AGG | GTA | GTG | GGG | GGG | TGT | 48 |
| Leu | Glu | Pro | Gln | Leu | Cys | Gly | Val | Val | Pro | Arg | Val | Val | Gly | Gly | Cys | |
| 1   |     |     |     | 5   |     |     |     |     | 10  |     |     |     |     | 15  |     | |

(2) INFORMATION FOR SEQ ID NO:40:

(i) SEQUENCE CHARACTERISTICS:
    (A) LENGTH: 16 amino acids
    (B) TYPE: amino acid
    (D) TOPOLOGY: linear (ii) MOLECULE TYPE: protein (xi) SEQUENCE DESCRIPTION: SEQ ID NO:40:

Leu Glu Pro Gln Leu Cys Gly Val Val Pro Arg Val Val Gly Gly Cys
 1               5                   10                  15

(2) INFORMATION FOR SEQ ID NO:41:

(i) SEQUENCE CHARACTERISTICS:
    (A) LENGTH: 105 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:41:

AGCTTCCACC ATGAAGTGCT CCTGGGTGAT CTTCTTCCTG ATGGCCGTGG TGACCGGCGT    60

GAACTCGCGA GATCTAGAGT CGACCTGCAG GATATCGAAT TCATT    105

(2) INFORMATION FOR SEQ ID NO:42:

(i) SEQUENCE CHARACTERISTICS:
    (A) LENGTH: 105 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:42:

GATCAATGAA TTCGATATCC TGCAGGTCGA CTCTAGATCT CGCGAGTTCA CGCCGGTCAC    60

CACGGCCATC AGGAAGAAGA TCACCCAGGA GCACTTCATG GTGGA    105

(2) INFORMATION FOR SEQ ID NO:43:

( i ) SEQUENCE CHARACTERISTICS:
    ( A ) LENGTH: 90 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:43:

TATGAAGACG TCGCCTCCTC ACTACTTCTG GAATAGCTCA GAGGCCGAGG CGGCCTCGGC    60

CTCTGCATAA ATAAAAAAAA TTAGTCAGGG    90

( 2 ) INFORMATION FOR SEQ ID NO:44:

( i ) SEQUENCE CHARACTERISTICS:
        ( A ) LENGTH: 90 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:44:

CGCCCTGACT AATTTTTTTT ATTTATGCAG AGGCCGAGGC CGCCTCGGCC TCTGAGCTAT    60

TCCAGAAGTA GTGAGGAGGC GACGTCTTCA    90

( 2 ) INFORMATION FOR SEQ ID NO:45:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:45:

AAGCGGCCGC GGCCATGCCG GCCACTAGTC TCGAGTT    37

( 2 ) INFORMATION FOR SEQ ID NO:46:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:46:

AACTCGAGAC TAGTGGCCGG CATGGCCGCG GCCGCTT    37

( 2 ) INFORMATION FOR SEQ ID NO:47:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:47:

CCCTTCCCTC GATACATTTC T    21

( 2 ) INFORMATION FOR SEQ ID NO:48:

( i ) SEQUENCE CHARACTERISTICS:

( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:48:

CCTTCCCTCG ATGCCACATT TC 22

( 2 ) INFORMATION FOR SEQ ID NO:49:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:49:

CCCCCCACA ACCCTTCCCT CTATTGCACC ACATTTCTTC GGCTCCAC 48

( 2 ) INFORMATION FOR SEQ ID NO:50:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:50:

CCCCCCACA ACCCTTCCGT CTATGTAACC ACATTTCTTC GGCTCCAC 48

( 2 ) INFORMATION FOR SEQ ID NO:51:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:51:

CACACCCCCC CACAATCCTT CCGTCTATGT AACCACATTT CTTCGGCTCC AC 52

( 2 ) INFORMATION FOR SEQ ID NO:52:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:52:

CAACCCTTGG ACCACATTTC T 21

( 2 ) INFORMATION FOR SEQ ID NO:53:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear (i i) MOLECULE TYPE: DNA (x i) SEQUENCE DESCRIPTION: SEQ ID NO:53:

ACCCTTGGAC CACCACATTT CT    22

(2) INFORMATION FOR SEQ ID NO:54:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:54:

GGGCCACACA CCCCCCCACT CCCCTAGGCA CAACTCCACA TAGCTCCGGC TCCAGTTGAG    60

G    61

(2) INFORMATION FOR SEQ ID NO:55:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:55:

GGCCACACAC CCCCCCACTC CCCTAGGCAC AACTCCACAT AGTTGCGGCT CCAGTTGAGG    60

(2) INFORMATION FOR SEQ ID NO: 56:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO: 56:

CACACACCCC CCCCTCCCC TAGGCACTAC TCCTTGTAGT TCTACACATT TCTTCGGCTCC    60

(2) INFORMATION FOR SEQ ID NO: 57:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:57:

CACCCCCCCA CAACCCTAGG TACAACACAT TTCTTCGGCT C    41

(2) INFORMATION FOR SEQ ID NO: 58:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO: 58:

CACCCCCCCA CAACCCTAGG GTATCCACAT TTCTTCGGCT                    40

( 2 ) INFORMATION FOR SEQ ID NO: 59:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 59:

CACCCCCCCA CAACCCTTCC ACTAGGACAT TTCTTCGG                      38

( 2 ) INFORMATION FOR SEQ ID NO: 60:

( i ) SEQUENCE CHARACTERISTICS:
        ( A ) LENGTH: 61 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 60:

CACACCCCCC CACAACCCTT GGGACTACTC CCTGACATTC TACACATTTC TTCGGCTCCA    60
C                                                                    61

( 2 ) INFORMATION FOR SEQ ID NO: 61:

( i ) SEQUENCE CHARACTERISTICS:
        ( A ) LENGTH: 58 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 61:

GGCCACACAC CCCCCCTTG GGACTACTCC CTGCAATTCT ACACATTTCT TCGGCTCC        58

( 2 ) INFORMATION FOR SEQ ID NO: 62:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 62:

CACCCCCCCA CTACCCTAGG CAC                                     23

( 2 ) INFORMATION FOR SEQ ID NO: 63:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 63:

CTGAGAGATA CACTTTCTTT TCTCCTTGAC CTGAT                         35

( 2 ) INFORMATION FOR SEQ ID NO: 64:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO: 64:

CTGAGAGATA CACTTTTCCT TGACCTGAT 29

( 2 ) INFORMATION FOR SEQ ID NO: 65:

( i ) SEQUENCE CHARACTERISTICS:
( A ) LENGTH: 32 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO: 65:

CTGAGAGATA CACTTTCTTT CCTTGACCTG AT 32

( 2 ) INFORMATION FOR SEQ ID NO: 66:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO: 66:

AGCTTCCCGG GATAGGTACC TCG 23

( 2 ) INFORMATION FOR SEQ ID NO: 67:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO: 67:

CGAGGTACCT ATCCCGGGA 19